United States Patent [19]

Teach

[11] Patent Number: 4,670,593
[45] Date of Patent: Jun. 2, 1987

[54] HALOACETAMIDINES AND THE HERBICIDAL USE THEREOF

[75] Inventor: Eugene G. Teach, El Cerrito, Calif.

[73] Assignee: Stauffer Chemical Co., Westport, Conn.

[21] Appl. No.: 668,122

[22] Filed: Nov. 5, 1984

Related U.S. Application Data

[63] Continuation of Ser. No. 512,862, Jul. 11, 1983, abandoned, which is a continuation of Ser. No. 272,860, Jun. 12, 1981, abandoned, which is a continuation-in-part of Ser. No. 91,854, Nov. 6, 1979, abandoned.

[51] Int. Cl.⁴ ............................................ C07C 123/00
[52] U.S. Cl. .............................. 564/245; 260/501.14; 260/501.12; 544/162; 544/163; 546/230; 546/231; 548/146; 548/215; 548/566; 564/48; 71/121; 71/120; 71/117; 71/115; 71/114; 71/95; 71/94; 71/90; 71/88; 71/76; 71/74; 71/73; 71/72
[58] Field of Search ........................... 71/121; 564/245

[56] References Cited

U.S. PATENT DOCUMENTS

| | | | |
|---|---|---|---|
| 3,153,670 | 10/1964 | Speziale et al. | 71/121 |
| 3,218,147 | 11/1965 | Homer | 71/121 |
| 3,284,289 | 11/1966 | Duerr et al. | 71/121 |
| 3,428,681 | 2/1969 | Kippur et al. | 564/225 |
| 3,547,621 | 12/1970 | Neighbors et al. | 71/121 |
| 4,093,655 | 6/1978 | Miller et al. | 71/121 |
| 4,209,319 | 6/1980 | Pissiotas et al. | 564/245 |

FOREIGN PATENT DOCUMENTS

| | | | |
|---|---|---|---|
| 2259221 | 12/1971 | Fed. Rep. of Germany | 71/121 |
| 2557651 | 6/1977 | Fed. Rep. of Germany | 564/245 |
| 4226286 | 12/1964 | Japan | 564/245 |

OTHER PUBLICATIONS

Speziale et al I, "The Reactions of, etc.," (1960), JACS 82, pp. 909–917 (1960).
Maringgele et al, "Reactions of Metal, etc.," (1979), CA 91:74669a, (1979).
England et al, "Nucleophilic Reactions, etc.," (1960), JACS 82, pp. 5116–5122 (1960).
Fokin et al, "Fluorination of Alkylamidine, etc.," (1978), cA 88:22104f, (1977).

Primary Examiner—Glennon H. Hollrah
Assistant Examiner—Amelia A. Owens
Attorney, Agent, or Firm—Harry A. Pacini

[57] ABSTRACT

Dichloroacetamidines having the formula

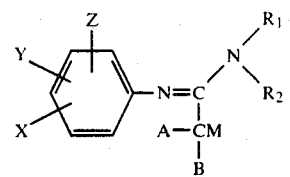

in which
A and B are independently selected from hydrogen, fluorine, chlorine, bromine and methyl, provided that at least one of A or B is other than hydrogen;
M is hydrogen or methyl;
X is selected from the group consisting of trifluoromethyl, lower alkyl, nitro, chloro, bromo, fluoro, cyano, lower alkoxy acetyl, lower alkylthio, trifluoromethylthio, and 3,3-diloweralkyl ureido;
Y is selected from the group consisting of hydrogen, lower alkyl, chloro, fluoro, nitro, trifluoromethyl, and lower alkoxy;
Z is selected from the group consisting of hydrogen and chloro;
$R_1$ is selected from the group consisting of hydrogen, alkyl and allyl;
$R_2$ is selected from the group consisting of alkyl, allyl, benzyl, hydroxyalkyl, alkynyl, N-alkyl amido, alkoxyalkyl, dialkoxyalkyl, alkoxy, cyano alkyl, substituted phenyl wherein the substituent is selected from the group trifluoromethyl, dichloro and 3,3-dimethylureido; and
$R_1$ and $R_2$ taken together with the nitrogen is selected from the group consisting of alkyl substituted oxazolidyl, morpholinyl, piperidinyl and pyrrolidinyl; and salts thereof; useful as herbicides.

14 Claims, No Drawings

HALOACETAMIDINES AND THE HERBICIDAL USE THEREOF

CROSS-REFERENCE TO RELATED APPLICATIONS

This is a continuation-in-part of Ser. No. 512,862 filed Jul. 11, 1983, which is a continuation of Ser. No. 272,860 filed Jun. 12, 1981, which is a continuation-in-part of Ser. No. 091,854 filed Nov. 6, 1979 all now abandoned.

This invention relates to certain novel haloacetamidines which are useful as herbicides. More specifically, this invention relates to a novel herbicidal compound known as acetamidines, more particularly dichloroacetamidines.

BACKGROUND OF THE INVENTION

1. Use of Herbicides

An herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate weed pests. They have gained a high degree of commercial success because it has been shown that such control increases crop yield and reduces harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the target weed. Certain herbicidal compounds are phytotoxic to some weed species but not to others.

The manufacturer of the herbicide recommends a range of rates and concentrations calculated to maximize weed control. The range of rates varies from approximately 0.01 to 50 pounds per acre, usually from 0.1 to 25 pounds per acre. The actual amount used depends upon several considerations including particular weed susceptibility and overall cost limitations.

2. Prior Art

U S. Pat. No. 3,153,670 relates primarily to vinyl amines. A utility disclosed for the vinyl amines is the preparation of amidines from primary amines. In U.S. Pat. No. 3,153,670 the following specific compounds are disclosed: N,N-diethyl-N'-phenyl 2,2-dichloroacetamidine, N,N-diethyl-N'-tolyl 2,2-dichloroacetamidine, N,N-diethyl-N'-p-chlorophenyl 2,2-dichloroacetamidine, N,N-diethyl-N'-p-nitrophenyl 2,2-dichloroacetamidine, and N,N-diethyl-N'-p-ethoxyphenyl 2,2-dichloroacetamidine. U.S. Pat. No. 3,153,670 generically discloses herbicidal utility for the above compounds. No specific testing or method of testing for herbicidal activity is set forth in the cited patent.

The *J. Am. Chem. Soc.* 82 902–9 (1960) discloses the compound N,N-diethyl-N'-phenyl 2,2-dichloroacetamidine.

U.S. Pat. No. 3,576,618 discloses certain N-trichloroacetamidines having the formula

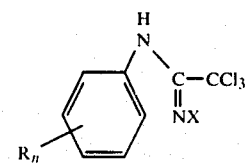

These compounds are useful as herbicides. The form taken by the compounds are the aryl amino form, thereby allowing only one substituent on the aryl amino nitrogen and always a hydrogen on the amino nitrogen with the phenyl moiety. These are commonly known as "reverse" acetamidines.

Similarly, West German Offenlegungschrift No. 2557651 relates to N-aryl-2,2-dihalo-acetamidine derivatives of the general formula

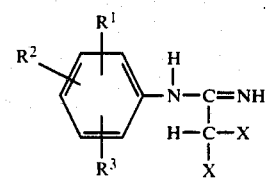

wherein $R^1$, $R^2$ and $R^3$ are the same or different and are defined as a hydrogen, halogen atom, aliphatic moiety or $R^4$—O— wherein $R^4$ is aliphatic or aromatic moiety and X is a halogen atom. These acetamidines are termed "reverse" acetamidines because of the tautomeric system within the molecule. The utility is disclosed as fungicidal.

The following are a group of patents which relate to acetamidines in which the two (2) positions substituted with a non-halogenated methyl group: U.S. Pat. No. 3,284,289, U.S. Pat. No. 3,487,156, U.S. Pat. No. 3,781,356, U.S. Pat. No. 3,781,357, U.S. Pat. No. 3,803,134 and U.S. Pat. No. 3,867,448.

The compounds disclosed in the above-cited U.S. patents are taught to be useful for the control of acarids and insects, combating undesired plant growth, harmful micro-organism, nematodes.

U.S. Pat. No. 3,428,681 relates to N-halotrichloroacetamidines having the general formula

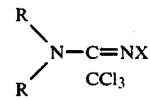

wherein X is chlorine, iodine or bromine and each R is independently selected from the group consisting of hydrogen, alkyl, aryl, cycloalkyl and heterocyclic. These compounds are disclosed as useful as bleaches and disinfectants, effective as fungicidal, herbicidal and algaecidal agents.

It is recognized the amidine compounds have the potential of existing in two geometrical isomeric forms, known as tautomers, in the aryl imino form [ArN=C(NHR)] and the aryl amino form [ArN=C(NR)]. Many compounds containing an "amidine moiety" possess potential for tautomerism, geometrical isomerism and conformational change. The "amidine moiety" refers to compounds containing the potentially tautomeric system —NH—C(X)=N— in which X is C, N, O or S as described by Jackman, L. M. et al., *J. Am. Chem. Soc.* 97 (10) 2811-18. In the present application the predominant tautomer is presumed to be in the imino form and the representation of the dichloro acetamidines will be in this form.

DESCRIPTION OF THE INVENTION

The compounds comprising the instant class of compound corresponds to the general formula

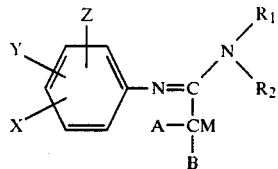

in which
- A and B are independently selected from the group consisting of hydrogen, fluorine, chlorine, bromine and methyl, provided that at least one of A or B is other than hydrogen; m is hydrogen or methyl;
- X is selected from the group consisting of trifluoromethyl, lower alkyl, nitro, chloro, bromo, fluoro, cyano, lower alkoxy acetyl, lower alkylthio, trifluoromethylthio, and 3,3-diloweralkyl ureido;
- Y is selected from the group consisting of hydrogen, lower alkyl, chloro, fluoro, nitro, trifluoromethyl, and lower alkoxy;
- Z is selected from the group consisting of hydrogen, and chloro;
- $R_1$ is selected from the group consisting of hydrogen, alkyl, and allyl;
- $R_2$ is selected from the group consisting of alkyl, allyl, benzyl, hydroxyalkyl, alkynyl, N-alkyl amido, alkoxyalkyl, dialkoxyalkyl, alkoxy, cyano alkyl, substituted phenyl wherein the substituent is selected from the group trifluoromethyl, dichloro and 3,3-dimethylureido; and
- $R_1$ and $R_2$ taken together with the nitrogen is selected from the group consisting of alkyl substituted oxazolidyl and alkyl substituted thiazolidyl, morpholinyl, piperidinyl and pyrrolidinyl; and salts thereof.

More particularly, with reference to the general formula above:
- A, B and M are as defined and X is selected from the group consisting of trifluoromethyl, lower alkyl having 1 to 3 carbon atoms, inclusive, nitro, chloro, bromo, fluoro, cyano, lower alkoxy having 1 to 3 carbon atoms, inclusive, acetyl, lower alkylthio having 1 to 3 carbon atoms, inclusive, trifluoromethylthio and 3,3-diloweralkyl ureido in which each lower alkyl has from 1 to 2 carbon atoms, inclusive;
- Y is selected from the group consisting of hydrogen, lower alkyl having 1 to 3 carbon atoms, inclusive, chloro, fluoro, nitro, trifluoromethyl and lower alkoxy having 1 to 3 carbon atoms, inclusive;
- Z is selected from the group consisting of hydrogen and chloro;
- $R_1$ is selected from the group consisting of hydrogen, alkyl having 1 to 6 carbon atoms, inclusive, and allyl;
- $R_2$ is selected from the group consisting of alkyl having 1 to 6 carbon atoms, inclusive, allyl, benzyl, hydroxyethyl, alkynyl having 3 to 4 carbon atoms, inclusive, N-alkylamido in which the alkyl has 1 to 3 carbon atoms, inclusive, alkoxyalkyl having 2 to 6 carbon atoms, inclusive, dialkoxyalkyl having 3 to 6 carbon atoms, inclusive, alkoxy having 1 to 4 carbon atoms, inclusive, cyanoalkyl having 2 to 4 carbon atoms, inclusive, substituted phenyl wherein said substituent is selected from the group trifluoromethyl, dichloro and 3,3-dimethylureido; and
- $R_1$ and $R_2$ taken together with the nitrogen is selected from the group consisting of alkyl substituted oxazolidyl and alkyl substituted thiazolidyl wherein said oxazolidyl or thiazolidyl is substituted 1, 2 or 3 times with alkyl having from 1 and 3 carbon atoms, inclusive, morpholinyl, piperidinyl and pyrrolidinyl; and
- salts thereof with an acid selected from the group consisting of HCl, HBr, HI, HF, $H_2SO_4$, $CCl_3COOH$, 2,4-dichlorophenoxy acetic acid, 3-amino-2,5-dichlorobenzoic acid, hexanoic acid, stearic acid, naphthalene acetic acid, pivalic acid, succinic acid, 10-undecenoic acid, benzoic acid, maleic acid and malonic acid.

The terms "lower alkyl" and "alkyl" includes straight chain and branched chain substituents of this type; the term "lower alkoxy" includes straight chain and branched chain substituents of this type; the term 'alkynyl' includes substituents of this type having straight or branched chain and at least one triple bond; the terms "alkoxy alkyl" and "dialkyloxy alkyl" include substituents of this type having a straight or branched chain configuration, and cyanoalkyl includes substituents having at least one cyano group (CN) and alkyl in straight or branched chain.

The compounds of this invention have been found to be active herbicides., that is, the compounds have been found to be herbicidally active against various species of weeds. In the broadest sense, the term "weeds" refers to plants which grow in locations in which they are not desired. As will be seen from the data which follows, these compounds show various activities as pre-emergence and/or post-emergence herbicides. In some cases they have been found to show particular activity against certain weed species.

This invention, therefore, also relates to a method of controlling undesirable vegetation comprising applying to such vegetation or the locus where such vegetation is found, a herbicidally effective amount of a compound as described herein, and also relates to herbicidal compositions of matter comprising a herbicidally effective amount of a compound as described herein plus an inert diluent or carrier suitable for use with herbicides.

As used herein, the term "herbicide" means a compound which controls or modifies the growth of plants, particularly of undesirable plants. By the term "herbicidally effective amount" is meant an amount of a compound which causes a controlling or modifying effect on the growth of treated plants. The term "plants" is meant to include germinant seeds, emerging seedlings and established vegetation including roots and the above ground portions. Such modifying and controlling effects include all deviations from natural development, for example, killing, retardation, defoliation, desiccation, regulation, stunting, tillering, stimulation, dwarfing and the like.

In general, the compounds of the present invention can be prepared by the following methods:

I. An appropriate substituted aniline (1) is reacted with an acyl chloride (2) to produce corresponding substituted anilide (3). The anilide is chlorinated with phosphorus chloride to prepare the substituted phenyl containing imidoyl chloride (4). A subsequent reaction with a secondary amine (4a) produces a substituted acetamidine (5) of the present invention. This sequence of reactions is depicted by the following equations:

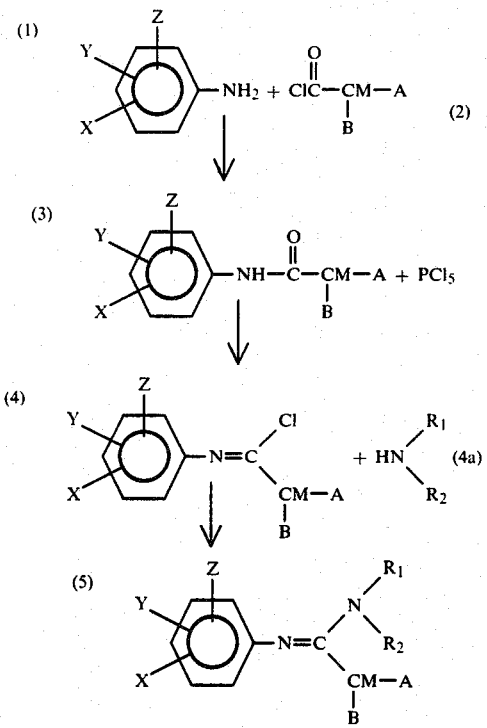

wherein A, B, M, $R_1$, $R_2$, X, Y and Z have the same significance as previously defined.

REACTION SCHEME I

II. An alternative reaction scheme is the reaction of an acylchloride (6) with a primary amine (7) to produce the corresponding amide (8). This reaction is followed by treatment of the amide (8) with phosphorus pentachloride in phosphorus oxychloride as a solvent to produce the imidoyl chloride (9). The imidoyl chloride is reacted with a substituted aniline to produce the substituted acetamidine (11a) or (11b) of the present invention. This sequence of reactions is depicted by the following equations:

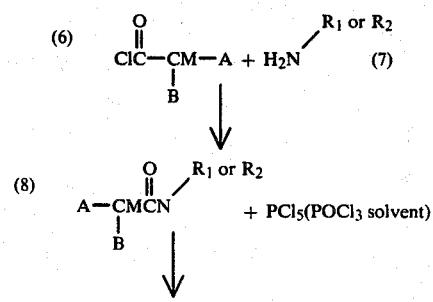

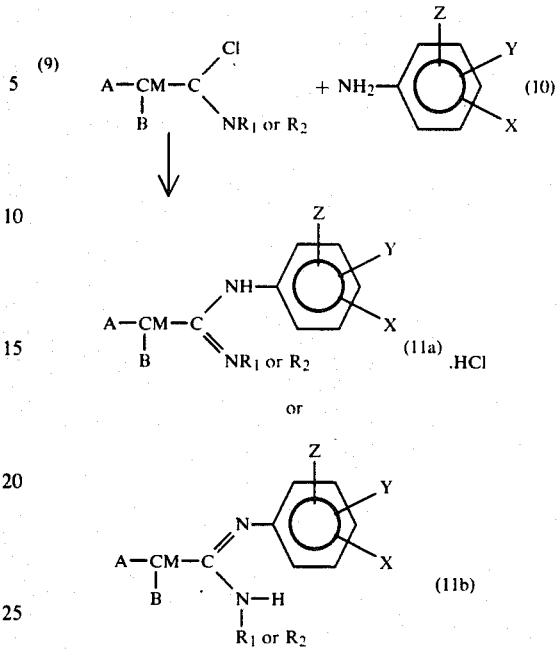

wherein A, B, M, $R_1$, $R_2$, X, Y and Z have the same significance as previously defined.

REACTION SCHEME II

In reaction schemes I and II, some of the individual reactions are performed in the presence of an organic solvent, such as acetone, methylene chloride and the like, where good chemical practice dictates. The reaction temperatures can vary from $-20°$ C. to $150°$ C. In many instances the reaction was exothermic. The reaction pressure may be atmospheric, subatmospheric or superatmospheric. However, for convenience of conducting the reactions, the pressure is generally atmospheric. The reaction time will, of course, vary depending upon the reactants and reaction temperature. Generally, the reaction time is from 0.25 to 24 hours, depending upon the steps and rate of reaction. After the reaction is complete, the product is recovered by separation from the by-products and the solvent removed as by evaporation, or distillation. The structure is confirmed by nuclear magnetic resonance or infrared spectra.

The following are representative illustrative examples for the preparation of the compounds of the present invention and requisite intermediates therefor. Following the examples is a table of compounds which are prepared according to the described procedures.

EXAMPLE A

Intermediate Preparation

3',5'-Dichloro-dichloroacetanilide 81 grams (0.5 mole) 3,5-dichloroaniline was dissolved in a flask containing 250 milliliters of reagent grade acetone. The solution was cooled to 0° C. and 74 grams (0.5 mole) dichloroacetyl chloride was added dropwise with vigorous stirring with the rate of addition adjusted to maintain the reaction temperature below 5° C.

When the addition was complete, 51 grams (0.50 mole) of triethylamine was immediately added dropwise with vigorous stirring, the addition rate adjusted to maintain the reaction temperature below 5° C. The reaction mixture was then allowed to attain ambient temperature and stirred at that temperature for one hour. The mixture was poured into water, the solid product filtered off and dried giving 126 grams (92.3% yield) of the desired product, a white. solid, m.p. 1323°–135° C.

EXAMPLE B

Intermediate Preparation

3',5'-Dichlorophenyldichloroacetimidoyl chloride 121 grams (0.44 mole) 3',5'-dichloro-dichloroacetanilide and 100 milliliters of phosphorous oxychloride were combined. Phosphorous pentachloride, 92.5 grams (0.44 mole), was added and the mixture was stirred virorously with heating at reflux until hydrogen chloride evolution ceased. The phosphorous oxychloride was stripped off at reduced pressure. Distillation gave 109.8 grams (85% yield) of 3',5'-dichlorophenyldichloroacetimidoyl chloride containing a small amount of solid. The b.p was 122°–126°/0.03 millimeters.

EXAMPIE 1A

N-3',5'-Dichlorophenyl-N'-isopropyldichloroacetamidine 10,2 grams (0.035 mol) 3',5'-dichlorophenyldichloroacetimidoyl chloride was dissolved in a flask containing 25 milliliters of methylene chloride and the solution cooled in an ice bath. 4.5 grams (0.076 mole) isopropyl amine was added dropwise while stirring vigorously and temperature maintained below 15° C. The reaction mixture was stirred at ambient temperature one hour, and washed with 100 milliliters water. The organic layer was separated, dried over magnesium sulfate and stripped at reduced pressure to yield 10.7 grams (97.3% yield) of N-3',5'-dichlorophenyl-N'-isopropyldichloroacetamidine, $n_d^{30}$ 1.5653.

EXAMPLE C

Intermediate Preparation

N-Isopropyldichloroacetamide

Dichloroacetyl chloride, 442.5 grams (3.0 mole), was dissolved in a flask containing 900 milliliters of methylene chloride and the solution cooled to 0° C. in an ice/acetone bath. 354 grams (5.98 mole) of isopropyl amine was added dropwise with vigorous stirring and the addition rate was adjusted to maintain the reaction temperature below 5° C. When the addition was complete, the mixture was allowed to stir at ambient temperature for one hour then washed with 2×500 milliliters water, the organic phase separated, dried over magnesium sulfate and stripped of solvent at reduced pressure giving 499 grams (98% yield) of the desired product, a white solid, m.p. 45°–48° C.

EXAMPLE D

Intermediate Preparation

N-Isopropyldichloroacetimidoyl chloride

N-isopropyldichloroacetamide, 249.5 grams (2.94 mole), and 210 milliliters of phosphorous pentachloride, 306.5 grams (2.94 mole), was added and the mixture was stirred vigorously and heated at reflux until hydrogen chloride evolution ceased. The phosphorous oxychloride was stripped off at reduced pressure. Distillation at 4.5 millimeters gave 360 grams (65% yield) of N-isopropyldichloroacetimidoyl chloride, b.p. 63°–72° C.

EXAMPLE 1B

Preparation via N-isopropyldichloroacetimidoyl chloride N-3',5'-Dichlorophenyl-N'-isopropyldichloroacetamidine 10.5 grams (0.065 mole) of 3,5-dichloroaniline was combined with 14.7 grams (0.078 mole) of N-isopropyl dichloroacetimidoyl chloride in a flask and heated to 30° C. The reaction proceeded to 48° C. and was heated again until it showed an exotherm. External heating was stopped and the reaction allowed to continue until it reached a peak exotherm of 150° C. and then allowed to cool to ambient temperature. While this reaction cooled, a second reaction using the same amounts and reagents was performed. This reaction was externally heated to 50° C. when it began to exotherm. A peak temperature of 140° C. was reached while the reaction flask was in an ice water bath. Both reaction mixtures were slurried in acetone, combined and diluted with ether and the solid hydrochloride filtered off. This yielded 42.2 grams (92.7% yield) of solid m.p. 201°–202° C. The entire amount was treated with 200 milliliters of 10% sodium hydroxide, extracted with 2×250 milliliters methylene chloride, the organic layer dried over magnesium sulfate and stripped of solvent under reduced pressure to give 36.5 grams (89% total yield) of an oil, $n_D^{30}$ of 1.5672.

EXAMPLE 2

N-3',5'-Dimethylphenyl-N'-isopropyldichloroacetamidine 3,5-dimethyl aniline, 8.9 grams (0.073 mole), and N-isopropyl dichloroacetimidoyl chloride, 15.8 grams (0.084 mole), were combined in a flask and the temperature immediately rose to 35° C. An ice bath was applied, and when the temperature reached 45° C., acetone was added to the bath. The exotherm ceased at 115° C., the ice bath was removed and the flask heated to 120° C. and maintained at that temperature until the mixture seemed homogeneous. A second reaction was run in the same manner, both were allowed to cool, slurried in ether, combined and filtered off as the solid hydrochloride m.p. 201°–203° C. The hydrochloride was then treated with 10% sodium hydroxide, extracted with methylene chloride and the organic phase dried over magnesium sulfate and the solvent stripped off at reduced pressure to give 33.1 grams (82.8% yield) of the desired produce with an $n_D^{30}$1.5382.

EXAMPLE 3

N-2,3-Dichlorophenyl-N'-isopropyldichloroacetamidine 9.7 grams (0.06 mole) of 2,3-dichloroaniline was combined with 13.6 grams (0.072 mole) N-isopropyldichloroacetimidoyl chloride and heated until the mixture started to exotherm. An ice bath was used to control but not stop, the exotherm. After the exotherm peaked, the flask and its contents were allowed to cool to ambient temperature and combined with a second reaction which was run in the same manner. These combined reactions were slurried in acetone, diluted with ether and the solid hydrochloride filtered off. The solid was then treated with 10% sodium hydroxide, extracted with methylene chloride, separated and the organic phase dried over magnesium sulfate. The solvent was then stripped off at reduced pressure to give 31.1 grams (82.7% yield) of the desired produce, an oil, $n_D^{30}$ 1.5668.

EXAMPLE 4

N-3-Chloro-2-methylphenyl-N'-isopropyldichloroacetamidine 3-chloro-2-methylaniline, 10 grams (0.035 mole), and N-isopropyldichloroacetimidoyl chloride, 7.9 grams (0.042 mole), were combined in a flask, heated to initiate the reaction and the rate of exotherm controlled, but not stopped, with the application of an ice bath. After the exotherm subsided, the reaction flask was allowed to cool to ambient temperature and the contents slurried with acetone diluted with ether. The solid product was filtered off giving 10.0 grams (97.7% yield) of the hydrochloride which decomposed at 236° C. 5 grams (0.015 mole) of this hydrochloride was treated with 10% sodium hydroxide to give 4.3 grams (0.014 mole) of an oil, $n_D^{30}$ 1.5440.

EXAMPLE 5

N-m-Trifluoromethylphenyl-N'-allyldichloroacetamidine

Allyl amine, 3 grams (0.053 mole), was dissolved in a flask containing 25 milliliters of methylene chloride. Meta-trifluoromethylphenyl dichloroacetimidoyl chloride, 7.6 grams (0.026 mole), was added dropwise while stirring and maintaining ambient temperature with a water bath. The mixture was allowed to stir one houre, washed with water, the organic phase separated and dried over magnesium sulfate and the solvent stripped at reduced pressure to give 6.9 grams (85.2% yield) of an oil, $n_D^{30}$ 1.4986.

EXAMPLE 6

N-m-Trifluoromethylphenyl-N',N'-tetramethylenedichloroacetamidine

Pyrrolidine, 3.6 grams (0.051 mole), was combined in a with 25 milliliters of methylene chloride. Metatrifluoromethylphenyl dichloroacetimidoyl chloride, 7.3 grams (0.025 mole), was added dropwise while stirring and maintaining ambient temperature with a water bath. The mixture was allowed to stir one hour at ambient temperature, washed with water, the organic layer dried over magnesium sulfate and stripped of solvent to give 8.0 grams (98.8% yield) of an oil $n_D^{30}$ 1.5140

EXAMPLE 7

4-(N-m-Trifluoromethylphenyl dichloroacetimidoyl) morpholine

Morpholine, 4.2 grams (0.0482 mole), was combined in a flask with 25 milliliters of methylene chloride. Metatrifluoromethylphenyl dichloroacetimidoyl chloride, 7 grams (0.024 mole), was added dropwise while stirring and maintaining ambient temperature with a water bath. The mixture was allowed to stir at ambient temperature one hour, then washed with water, the organic phase separated, dried over magnesium sulfate and the solvent stripped off at reduced pressure to give 7.3 grams (89% yield) of an oil, $_D^{30}$ 1.5184.

EXAMPLE 8

(N-m-Trifluoromethylphenyl dichloroacetimidoyl 2,2,5-trimethyl oxazolidine

Twenty-two milliliters (0.048 mole) of a solution of 2,2,5-trimethyl oxazolidine in benzene (4 milliliters = 1 gram in benzene) was combined in a flask with 15 milliliters liters of methylene chloride. Meta-trifluoromethylphenyl dichloroacetimidoyl chloride, 6.7 grams (0.023 mole), was added dropwise while stirring and maintaining ambient temperature with a water bath. The mixture was allowed to stir at ambient temperature one hour, washed with water, the organic layer separated, dried over magnesium sulfate and stripped of solvent to give 6.5 grams (76.5% yield) of an oil, $n_D^{30}$ 1.4818.

EXAMPLE 9

Preparation of Intermediate

N-Isopropyl chlorofluoroacetamide

A solution of 11.8 grams (0.2 mole) isopropyl amine in 20 milliliters ethyl alcohol were added dropwise at 10°–15° C. with stirring to a solution of ethyl fluorochloroacetate and 5 drops of ethylene glycol in 80 milliliters ethyl alcohol. The solution was stirred at 10°–20° C. for 2 hours and was then stored at −15° C. for 3 days. At this time, the solution was evaporated to leave a liquid, 25.2 grams, $n_D^{30}$ 1.4395, identified as the title compound by infrared and nuclear magnetic resonance spectroscopy.

Preparation of Intermediate

N-Isopropyl chlorofluoroacetamide

In a 100 milliliter flask were placed 22 grams (0.14 mole) of N-isopropyl chlorofluoroacetamide and 3 milliliters of phosphorous oxychloride. Pulverized phosphorous pentachloride, 30.0 grams (0.14 mole), was added to this mixture at an initial temperature of 32° C. The temperature rose to 42° C. over the course of the addition. After all the phosphorous pentachloride had been added, the mixture was heated. The maJority of the hydrogen chloride was evolved at 40° C. and by the time the temperature reached reflux (120° C.), gas evolution had ceased. The mixture was next distilled at atmospheric pressure using a 15 centimeter glass - helix packed column with attached variable takeoff condenser to give 17.8 grams of product, b.p. 136°–138° C., identified as the title compound by infrared and nuclear magnetic resonance spectroscopy.

N-(3,5-Dimethylphenyl)-N'-isopropyl chlorofluoroacetamidine

In a 100 milliliter flask was placed 5.0 grams (0.03 mole) of N-isopropylchlorofluoroacetimidoyl chloride. A thermometer and air-cooled condenser were attached to the flask. To this was added 2.8 grams (0.02 mole) of 3,5-dimethylaniline. There was an immediate increase in temperature and formation of a white solid. When the temperature reached 70° C., a cold bath was applied to moderate the reaction and when no further isotherm was observed, the mixture was heated to 140° C. with a heat-gun.

The mixture was then allowed to return to room temperature and the resulting dark oil was taken up in acetone, addition of pentane caused a solid to separate which was removed by filtration. This solid was mixed with 50 mililiters methylene chloride and shaken with 50 milliliters of 10% sodium hydroxide. The organic layer was separated, washed twice with 50 milliliters portion of water and dried over magnesium sulfate.

Removal of solvent in vacuum left an oil, 3.6 grams, $n_D^{30}$ 1.5229, which was identified by infrared and nuclear magnetic resonance spectroscopy to be the title compound. The oil eventually crystallized to a solid of m.p. 37°–40° C.

EXAMPLE 10

N-(2,3-Dichlorophenyl)-N'-isopropyl chlorofluoroacetamidine

The above procedure was repeated with 5.0 grams (0.03 mole) N-isopropylchlorofluoroacetimidoyl chloride and 3.7 grams (0.02% mole) of 2,3-dichloroaniline to yield 3.7 grams of a dark oil, identified by infrared and nuclear magnetic resonance spectroscopy to be the title compound.

EXAMPLE 11

N-(3,5-Dichlorophenyl)-N'-isopropyl chlorofluoroacetamidine

The above procedure was repeated with 5.0 grams (0.03 mole) N-isopropylchlorofluoroacetimidoyl chloride and 3.7 grams (0.02 mole) of 3,5-dichloroaniline to yield 4.9 grams of an oil, $n_D^{30}$ 1.5540, identified by infrared and nuclear magnetic resonance spectroscopy as the title compound.

EXAMPLE 12

Preparation of Intermediate

N-Isopropylbromofluoro acetamide

A solution of 14.8 grams (0.25 mole) isopropyl amine in 25 milliliters ethanol was added dropwise to a solution of ethyl bromofluoroacetate, 40 grams (0.22 mole), and 5 drops ethylene glycol in 100 milliliters ethyl alcohol at 10°–15° C. The solution was stirred at 10°–20° C. for 2 hours and was then stored at −15° C. for 3 days. At this time, the solution was evaporated to leave a liquid, 41.8 grams, $n_D^{30}$ 1,4629, identified by infrared spectroscopy as the title compound.

Preparation of Intermediate

N-Isopropylbromofluoroacetimidoyl bromide

In a 100 milliliter flask fitted with a gas-inlet, thermometer, magnetic stirrer and reflux condenser were placed 20.0 grams (0.1 mole) of N-isopropylbromofluoroacetimidoyl bromide. Argon was flushed through the system and after 15 minutes, 27.3 grams (0.1 mole) of phosphorous tribromide were added in one portion. The temperature rose to 48° C. Cooling was applied with an ice bath and bromide, 1.1 grams (0.1 mole) was added slowly with stirring. After addition was complete, the mixture was allowed to come to room temperature and after one hour it was heated to 85°–90° C. The argon purge was maintained throughout the heating period. After 1½ hours the evolution of HBr had ceased and the mixtrue was cooled to 10° C. and filtered free of phosphorous oxybromide. The filtrate was vacuum distilled to yield 16.4 grams, b.p. 53°–60° C. at 1 millimeter. Identified by infrared spectroscopy as the title compound.

N-(b 3,5-Dichlorophenyl)-N'-isopropyl bromofluoroacetamidine

In a 100 milliliter flask was placed 5.0 grams (0.02 mole) of the above imidoyl bromide. A thermometer and air cooled condenser were attached to the flask. To this was added 3.1 grams (0.02 mole) of 3,5-dichloroaniline. The temperature rose slowly to 70° C., and at 70° C. an ice bath was used to moderate the reaction. When no further exotherm was observed, the mixture was heated to 135° C. and was then allowed to cool. The residue was taken up in 50 milliliters methylene chloride and this solution was carefully shaken with 50 milliliters of 10% sodium hydroxide solution. The organic layer was then shaken with 50 milliliters of a saturated salt solution and dried. Removal of solvent in vacuum left an oil, 2.9 grams, identified by infrared and nuclear magnetic resonance spectroscopy as the title compound.

EXAMPLE 13

Preparation of Intermediate

N-Isopropyldifluoroacetamide

A solution of 20 grams (0.16 mole) of ethyl difluoroacetate in 20 milliliters ethyl alcohol was added slowly in a solution of 9.5 grams (0.16 mole) isopropylamine amine and 5 drops of ethylene glycol in 30 milliliters ethyl alcohol. The temperature rose slowly to 27° C. The mixture was then refluxed for 3 days. After this reflux period, the solution was evaporated at 100 millimeters and the residue was distilled at atmospheric pressure to yield 18.0 grams, b.p. 86°–88°, identified by infrared spectroscopy as the title compound.

N-Isopropyldifluoroacetimidoyl bromide

In a 100 milliliter flask fitted with thermometer, gas-inlet, and magnetic stirrer was placed 12.0 grams (0.09 mole) of N-isopropyldifluoroacetamide. Argon was flushed through the system and phosphorous tribromide, 27.3 grams (0.09 mole), was added slowly at 10°–15° C. Bromine, 14.0 grams (0.09 mole), was then added slowly at 10°–15° C. with stirring. After all the bromine was added, the mixture was allowed to come to room temperature and was then heated with argon sweep at 85°–90° C. Heating was continued for 2 hours. The mixture was next cooled to 0° C. and filtered free of phosphorous oxybromide. The filtrate was vacuum distilled to yield 4.0 grams, b.p. 34°–38° (50 millimeters identified by infrared spectroscopy as the title compound.

N-(3,5-Dichlorophenyl)-N-isopropyldifluoroacetamidine

A solution of 3.2 grams (0.02 mole) of 3,5-dichloroaniline in 50 milliliters toluene was heated to reflux (111° C.) and 4.0 grams (0.02 mile) of N-isopropyldifluoroacetimidoyl bromide was added slowly. A vigorous reaction occurred with separation of solid. The mixture was refluxed for ½ hour after addition was complete, cooled and filtered to give 6.0 grams of the hydrobromide salt. The solid was slurried in 50 milliliters methylene chloride in a separatory funnel and this mixture was shaken with cold 5% sodium hydroxide solution. The mixture was phase-separated and washed with two 50 milliliter portions of water. Evaporation of solvent after drying left 3.9 grams of a liquid, $n_D^{30}$ 1.5425, identified by infrared and nuclear magnetic resonance spectroscopy as the title compound.

Dichloroacetamidine Salt Examples

EXAMPLE 14

Trifluoroacetic Acid Salt of N-(3,5-Dichlorophenyl)-N'-isopropyl dichloroacetamidine The amidine (3.1 grams, 0.01 mole) and the trifluoroacetic acid (1.1 grams, 0.01 mole) were combined in 35 milliliters ethyl ether and the mixture allowed to stir overnight at room temperature, refluxed for 45 minutes and the solvent removed in vacuo. The product was a very viscous semi-solid. Yield: 2.0 grams (47.6%). Infrared indicated the product was the expected salt.

EXAMPLE 15

Composition of Pivalic Acid and N-(3,5-Dichlorophenyl-N'-isopropyl dichloroacetamidine The amidine (3.1 grams, 0.01 mole) and pivalic acid (1.0 grams, 0.1 mole) were combined in 35 milliliters tetrahydrofuran. The mixture was stirred ½ hour at room temperature and refluxed 2 hours. The solvent was removed giving a tan oil, $n_D^{30}$ 1.5192. Yield: 4.0 grams (97.5%). Infrared indicated a composition of pivalic acid and amidine.

EXAMPLE 16

Composition of 10-Undecenoic Acid and N-(3,5-Dichlorophenyl)-N'-isopropyl dichloroacetamidine Same procedure as in Example 15. There was obtained a tan oil, $n_D^{30}$ 1.5163. Yield: 4.5 grams (91.8%). Infrared confirmed the expected title composition.

EXAMPLE 17

Composition of Succinic Acid and N-(3,5-Dichlorophenyl)-N'-isopropyl dichloroacetamidine Same procedure as in Example 15 using the acetamidine (3.1 grams, 0.01 mole) and succinic acid (0.6 grams, 005 mole). Viscous semi-solid. Yield: 2.1 grams (56.8%). Infrared confirmed the expected title composition.

The following is a table of compounds which are prepared according to the aforementioned procedures. Compound numbers have been assigned to them and are used for identification throughout the balance of the specification.

TABLE I

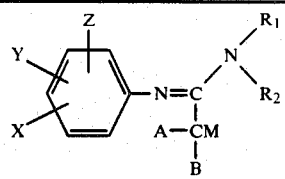

| Compound Number | —CMAB | X | Y | Z | $R_1$ | $R_2$ | m.p. °C. or $n_D^{30}$ |
|---|---|---|---|---|---|---|---|
| 1 | —CHCl$_2$ | 3-CF$_3$ | H | H | —CH$_2$CH=CH$_2$ | —CH$_2$CH=CH$_2$ | 1.5002 |
| 2 | —CHCl$_2$ | 3-CF$_3$ | H | H | H | t-C$_4$H$_9$ | 1.4754 |
| 3 | —CHCl$_2$ | 3-CF$_3$ | H | H | | 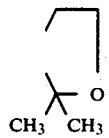 | 1.4990 |
| 4 | —CHCl$_2$ | 3-CF$_3$ | H | H | H | 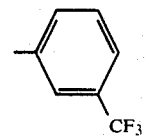 | 1.5083 |
| 5 | —CHCl$_2$ | 3-CF$_3$ | H | H | H | —C$_3$H$_7$ | 1.4810 |
| 6 | —CHCl$_2$ | 3-CF$_3$ | H | H | H | —C$_4$H$_9$ | 1.4833 |
| 7 | —CHCl$_2$ | 3-CF$_3$ | H | H | H | 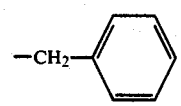 | 1.5310 |
| 8 | —CHCl$_2$ | 3-CF$_3$ | H | H | H | 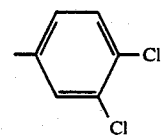 | 1.5650 |
| 9 | —CHCl$_2$ | 3-CF$_3$ | H | H | H | —C$_6$H$_{13}$ | 1.4823 |
| 10 | —CHCl$_2$ | 3-CF$_3$ | H | H | H | —C$_2$H$_4$OH | 1.5021 |

TABLE I-continued

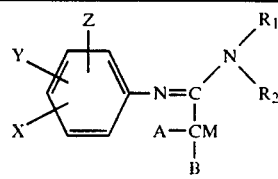

| Compound Number | —CMAB | X | Y | Z | R₁ | R₂ | m.p. °C. or $n_D^{30}$ |
|---|---|---|---|---|---|---|---|
| 11 | —CHCl₂ | 3-CF₃ | H | H | H | 2-methylphenyl-NHC(=O)N(CH₃)₂ | Glass |
| 12 | —CHCl₂ | 3-CF₃ | H | H | H | —C₅H₁₁ | 1.4800 |
| 13 | —CHCl₂ | 3-CF₃ | H | H | H | —i-C₄H₉ | 1.4760 |
| 14 | —CHCl₂ | 3-CF₃ | H | H | H | —i-C₄H₉ | 1.4770 |
| 15 | —CHCl₂ | 3-CF₃ | H | H | H | —i-C₃H₇ | 1.4770 |
| 16 | —CHCl₂ | 3-CF₃ | H | H | —C₂H₅ | —C₂H₅ | 1.4890 |
| 17 | —CHCl₂ | 3-CF₃ | H | H | H | —CH₂CH=CH₂ | 1.4986 |
| 18 | —CHCl₂ | 3-CF₃ | H | H | H | —C₂H₅ | 1.4873 |
| 19 | —CHCl₂ | 3-CF₃ | H | H | \-(R₁,R₂ = pyrrolidinyl)- | | 1.5140 |
| 20 | —CHCl₂ | 3-CF₃ | H | H | \-(R₁,R₂ = morpholinyl)- | | 1.5184 |
| 21 | —CHCl₂ | 3-CF₃ | H | H | \-(R₁,R₂ = 2,2,6-trimethyl-tetrahydro-1,3-oxazine)- | | 1.4818 |
| 22 | —CHCl₂ | 3-CF₃ | H | H | \-(R₁,R₂ = 2,2-dimethyl-thiazine)- | | 1.4948 |
| 23 | —CHCl₂ | 3-CF₃ | H | H | H | —C(=O)NHCH₃ | 1.4678 |
| 24 | —CH₂Cl | 3-CF₃ | H | H | H | —C₃H₇ | 1.4810 |
| 25 | —CH₂Cl | 2-C₂H₅ | 6-C₂H₅ | H | H | —C₃H₇ | 1.5100 |
| 26 | —CH₂Cl | 2-C₂H₅ | 6-C₂H₅ | H | H | —i-C₃H₇ | 1.5212 |
| 27 | —CH₂Cl | 2-C₂H₅ | 6-C₂H₅ | H | H | —C₄H₉ | 1.5103 |
| 28 | —CH₂Cl | 2-C₂H₅ | 6-C₂H₅ | H | H | —i-C₄H₉ | 1.5090 |
| 29 | —CH₂Cl | 2-C₂H₅ | 6-C₂H₅ | H | H | —s-C₄H₉ | 1.5021 |
| 30 | —CH₂Cl | 2-C₂H₅ | 6-C₂H₅ | H | —C₂H₅ | —C₂H₅ | 1.5150 |
| 31 | —CH₂Cl | 2-C₂H₅ | 6-C₂H₅ | H | H | —CH₂CH=CH₂ | 1.5230 |
| 32 | —CH₂Cl | 2-C₂H₅ | 6-C₂H₅ | H | H | —C₅H₁₁ | 1.5032 |
| 33 | —CH₂Cl | 2-C₂H₅ | 6-C₂H₅ | H | H | —C(CH₃)₂C≡CH | 1.5160 |
| 34 | —CH₂Cl | 2-C₂H₅ | 6-C₂H₅ | H | \-(R₁,R₂ = piperidinyl)- | | 1.5322 |
| 35 | —CH₂Cl | 2-C₂H₅ | 6-C₂H₅ | H | —C₃H₇ | —C₃H₇ | 1.5010 |
| 36 | —CH₂Cl | 2-C₂H₅ | 6-C₂H₅ | H | H | —CH(CH₃)CH₂(CH₃)₂ | 1.4900 |
| 37 | —CH₂Cl | 2-C₂H₅ | 6-C₂H₅ | H | —CH₂CH=CH₂ | —CH₂CH=CH₂ | 1.5180 |

TABLE I-continued

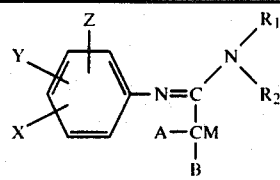

| Compound Number | —CMAB | X | Y | Z | R₁ | R₂ | m.p. °C. or $n_D^{30}$ |
|---|---|---|---|---|---|---|---|
| 38 | —CH₂Cl | 2-C₂H₅ | 6-C₂H₅ | H | | (tetrahydropyranyl) | 1.5323 |
| 39 | —CH₂Cl | 2-C₂H₅ | 6-C₂H₅ | H | H | (2,2-dimethyl-1,3-dioxolanyl) | 1.5308 |
| 40 | —CH₂Cl | 2-C₂H₅ | 6-C₂H₅ | H | H | —CH₂CH(OCH₃)₂ | 1.5018 |
| 41 | —CH₂Cl | 2-C₂H₅ | 6-C₂H₅ | H | —CH₃ | —OCH₃ | 1.5110 |
| 42 | —CH₂Cl | 2-C₂H₅ | 6-C₂H₅ | H | H | —CH₂C≡N | Glass |
| 43 | —CHCl₂ | 3-CF₃ | 4-Cl | H | H | —C₂H₅ | 1.5133 |
| 44 | —CHCl₂ | 3-CF₃ | 4-Cl | H | H | —C₃H₇ | 1.5073 |
| 45 | —CHCl₂ | 3-CF₃ | 4-Cl | H | H | —i-C₃H₇ | 1.5035 |
| 46 | —CHCl₂ | 3-CF₃ | 4-Cl | H | H | —CH₂CH=CH₂ | 1.5181 |
| 47 | —CHCl₂ | 3-CF₃ | 4-Cl | H | H | —c-C₃H₅ | 1.5226 |
| 48 | —CHCl₂ | 3-CF₃ | 4-Cl | H | H | —C₄H₉ | 1.5058 |
| 49 | —CHCl₂ | 3-CF₃ | 4-Cl | H | H | —i-C₄H₉ | 1.4980 |
| 50 | —CHCl₂ | 3-CF₃ | 4-Cl | H | H | —s-C₄H₉ | 1.4963 |
| 51 | —CHCl₂ | 3-CF₃ | 4-Cl | H | H | —t-C₄H₉ | 1.4923 |
| 52 | —CHCl₂ | 3-CF₃ | 4-Cl | H | C₂H₅ | —C₂H₅ | 1.5172 |
| 53 | —CHCl₂ | 3-CF₃ | 4-Cl | H | H | —(CH₂)₂OCH₃ | 1.5060 |
| 54 | —CHCl₂ | 3-CF₃ | 4-Cl | H | H | —SC₂H₅ | 1.5268 |
| 55 | CCl₂CH₃ | 3-CF₃ | H | H | H | —C₃H₇ | 1.4768 |
| 56 | CCl₂CH₃ | 3-CF₃ | H | H | H | —C₄H₉ | 1.4700 |
| 57 | —CHCl₂ | 3-CF₃ | H | H | H | —c-C₃H₅ | 1.4960 |
| 58 | —CHCl₂ | 3-CF₃ | H | H | H | —CH₂)₂OCH₃ | 1.4840 |
| 59 | —CHCl₂ | 3-CF₃ | H | H | H | —C(CH₃)₂C₂H₅ | 1.4733 |
| 60 | —CHCl₂ | 3-CF₃ | H | H | H | —CH₂CH(OCH₃)₂ | 1.4764 |
| 61 | —CHCl₂ | 3-CF₃ | 5-CF₃ | H | H | —i-C₃H₇ | 1.4382 |
| 62 | —CHCl₂ | 4-Cl | H | H | H | —i-C₃H₇ | 1.4222 |
| 63 | —CHCl₂ | 3-CF₃ | 5-CF₃ | H | H | —C₂H₅ | 1.4498 |
| 64 | —CHCl₂ | 3-CF₃ | 5-CF₃ | H | H | —C₃H₇ | 1.4487 |
| 65 | —CHCl₂ | 3-CF₃ | 5-CF₃ | H | H | —CH₂CH=CH₂ | 1.4580 |
| 66 | —CHCl₂ | 3-CF₃ | 5-CF₃ | H | H | —c-C₃H₅ | 1.4600 |
| 67 | —CHCl₂ | 3-CF₃ | 5-CF₃ | H | H | —C₄H₉ | 1.4483 |
| 68 | —CHCl₂ | 3-CF₃ | 5-CF₃ | H | H | —i-C₄H₉ | 1.4482 |
| 69 | —CHCl₂ | 3-CF₃ | 5-CF₃ | H | H | —s-C₄H₉ | 1.4460 |
| 70 | —CHCl₂ | 3-CF₃ | 5-CF₃ | H | H | —(CH₂)₂OCH₃ | m.p. 68-71° C. |
| 71 | —CHCl₂ | 3-CF₃ | 5-CF₃ | H | H | —(CH₂CH(OCH₃)₂ | 1.4490 |
| 72 | —CHCl₂ | 3-CF₃ | 5-CF₃ | H | CH₃ | —OCH₃ | 1.4504 |
| 73 | —CHCl₂ | 3-CF₃ | 5-CF₃ | H | C₂H₅ | —C₂H₅ | 1.4574 |
| 74 | —CHCl₂ | 3-NO₂ | 5-CF₃ | H | H | —C₂H₅ | 1.5653 |
| 75 | —CHCl₂ | 3-NO₂ | 5-CF₃ | H | H | —i-C₃H₇ | 1.5498 |
| 76 | —CHCl₂ | 3-NO₂ | 5-CF₃ | H | H | —C₃H₇ | 1.5547 |
| 77 | —CHCl₂ | 3-NO₂ | 5-CF₃ | H | H | —CH₂CH=CH₂ | 1.5638 |
| 78 | —CHCl₂ | 3-NO₂ | 5-CF₃ | H | H | —i-C₄H₉ | 1.5437 |
| 79 | —CHCl₂ | 3-NO₂ | 5-CF₃ | H | H | —s-C₄H₉ | 1.5410 |
| 80 | —CHCl₂ | 3-NO₂ | 5-CF₃ | H | H | —(CH₂)₂OCH₃ | 1.5540 |
| 81 | —CHCl₂ | 3-Cl | 4-Cl | H | H | —C₂H₅ | 1.5560 |
| 82 | —CHCl₂ | 3-Cl | 4-Cl | H | H | —C₃H₇ | 1.5575 |
| 83 | —CHCl₂ | 3-Cl | 4-Cl | H | H | —i-C₃H₇ | m.p. 62-65° C. |
| 84 | —CHCl₂ | 3-Cl | 4-Cl | H | H | —CH₂CH=CH₂ | 1.5700 |
| 85 | —CHCl₂ | 3-CF₃ | H | H | H | —N(CH₃)₂ | 1.5198 |
| 86 | —CHCl₂ | 3-CF₃ | 4-Cl | H | H | —CH₃ | 1.5401 |
| 87 | —CHCl₂ | 3-Cl | 4-Cl | H | H | —i-C₄H₉ | 1.5643 |
| 88 | —CHCl₂ | 3-Cl | 4-Cl | H | H | —s-C₄H₉ | 1.5643 |
| 89 | —CHCl₂ | 3-Cl | 4-Cl | H | H | —(CH₂)₂OCH₃ | 1.5770 |
| 90 | —CHCl₂ | 3-Cl | 4-Cl | H | —CH₃ | —OCH₃ | 1.5810 |
| 91 | —CHCl₂ | 3-Cl | 5-Cl | H | H | —C₂H₅ | 1.5818 |
| 92 | —CHCl₂ | 3-Cl | 5-Cl | H | H | —C₃H₇ | 1.5723 |
| 93 | —CHCl₂ | 3-Cl | 5-Cl | H | H | —i-C₃H₇ | 1.5653 |
| 94 | —CHCl₂ | 3-Cl | 5-Cl | H | H | —CH₂CH=CH₂ | 1.5850 |
| 95 | —CHCl₂ | 3-Cl | 5-Cl | H | H | —s-C₄H₉ | 1.5613 |
| 96 | —CHCl₂ | 3-Cl | 5-Cl | H | H | —CH₂CH₂OCH₃ | m.p. 67-70° C. |
| 97 | —CHCl₂ | 3-Cl | 5-Cl | H | —CH₃ | —OCH₃ | 1.5770 |

TABLE I-continued

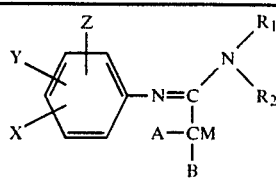

| Compound Number | —CMAB | X | Y | Z | R₁ | R₂ | m.p. °C. or $n_D^{30}$ |
|---|---|---|---|---|---|---|---|
| 98 | —CHCl₂ | 3-Cl | H | H | H | —C₂H₅ | 1.5730 |
| 99 | —CHCl₂ | 3-Cl | H | H | H | —C₃H₇ | 1.5669 |
| 100 | —CHCl₂ | 3-Cl | H | H | H | —i-C₃H₇ | 1.5620 |
| 101 | —CHCl₂ | 3-Cl | H | H | H | —CH₂CH=CH₂ | 1.5831 |
| 102 | —CHCl₂ | 3-Cl | H | H | H | —i-C₄H₉ | 1.5578 |
| 103 | —CHCl₂ | 3-Cl | H | H | H | —s-C₄H₉ | 1.5555 |
| 104 | —CHClCH₃ | 3-CF₃ | H | H | H | —C₃H₇ | 1.4989 |
| 105 | —CHClCH₃ | 3-CF₃ | H | H | H | —i-C₃H₇ | 1.4904 |
| 106 | —CHCl₂ | 3-Cl | 5-Cl | H | H | —i-C₄H₉ | 1.5620 |
| 107 | —CHCl₂ | 3-CF₃ | H | H | H | —CH(C₂H₅)CH₂OCH₃ | 1.4974 |
| 108 | —CHCl₂ | 3-Cl | H | H | H | —CH₂CH₂OCH₃ | 1.4915 |
| 109 | —CHCl₂ | 3-Cl | H | H | —CH₃ | —OCH₃ | 1.5700 |
| 110 | —CHClCH₃ | 3-CF₃ | H | H | H | —CH₂CH=CH | 1.5057 |
| 111 | —CHClCH₃ | 3-CF₃ | H | H | H | —i-C₄H₉ | 1.4915 |
| 112 | —CHClCH₃ | 3-CF₃ | H | H | H | —C₄H₉ | 1.4893 |
| 113 | —CHClCH₃ | 3-CF₃ | H | H | H | —(CH₂)₂OCH₃ | 1.4957 |
| 114 | —CHCl₂ | 2-Cl | 5-CF₃ | H | H | —C₂H₅ | 1.5170 |
| 115 | —CHCl₂ | 2-Cl | 5-CF₃ | H | H | —i-C₃H₇ | 1.5090 |
| 116 | —CHCl₂ | 2-CF₃ | 4-Cl | H | H | —C₂H₅ | 1.5273 |
| 117 | —CHCl₂ | 2-CF₃ | 4-Cl | H | H | —i-C₃H₇ | m.p. 80–82° C. |
| 118 | —CHCl₂ | 3-NO₂ | 4-Cl | H | H | —C₂H₅ | m.p. 82–84° C. |
| 119 | —CHCl₂ | 3-NO₂ | 4-Cl | H | H | —i-C₃H₇ | 1.5810 |
| 120 | —CHCl₂ | 3-SCF₃ | H | H | H | —C₂H₅ | 1.5320 |
| 121 | —CHCl₂ | 3-SCF₃ | H | H | H | —i-C₃H₇ | 1.5810 |
| 122 | —CHCl₂ | 3-NHCN(CH₃)₂ (C=O) | H | H | H | —i-C₃H₇ | Glassy solid |
| 123 | —CHCl₂ | 2-CF₃ | H | H | H | —C₂H₅ | 1.5140 |
| 124 | —CHCl₂ | 2-CF₃ | H | H | H | —i-C₃H₇ | 1.5054 |
| 125 | —CHCl₂ | 3-CH₃ | 5-CH₃ | H | H | —C₂H₅ | m.p. 75–78° C. |
| 126 | —CHCl₂ | 3-CH₃ | 5-CH₃ | H | H | —i-C₃H₇ | 1.5310 |
| 127 | —CHCl₂ | 2-Cl | 3-Cl | H | H | —C₂H₅ | 1.5823 |
| 128 | —CHCl₂ | 2-Cl | 3-Cl | H | H | —i-C₃H₇ | 1.5650 |
| 129 | —CHCl₂ | 2-Cl | 4-Cl | H | H | —C₂H₅ | 1.5790 |
| 130 | —CHCl₂ | 2-Cl | 4-Cl | H | H | —i-C₃H₇ | 1.5700 |
| 131 | —CHCl₂ | 2-Cl | 6-Cl | H | H | —C₂H₅ | 1.5728 |
| 132 | —CHCl₂ | 2-Cl | 2-Cl | H | H | —i-C₃H₇ | 1.5590 |
| 133 | —CHCl₂ | 3-CN | H | H | H | —C₂H₅ | 1.5673 |
| 134 | —CHCl₂ | 3-CN | H | H | H | —i-C₃H₇ | 1.5620 |
| 135 | —CHCl₂ | 2-CH₃ | 6-CH₃ | H | H | —C₂H₅ | 1.5450 |
| 136 | —CHCl₂ | 2-C₂H₅ | 6-C₂H₅ | H | H | —C₂H₅ | 1.5410 |
| 137 | —CHCl₂ | 3-NO₂ | 5-NO₂ | H | H | —C₂H₅ | m.p. 110–112° C. |
| 138 | —CHCl₂ | 3-NO₂ | 5-NO₂ | H | H | —i-C₃H₇ | m.p. 132–134° C. |
| 139 | —CHCl₂ | 2-NO₂ | 4-CF₃ | H | H | —C₂H₅ | 1.5180 |
| 140 | —CHCl₂ | 2-NO₂ | 4-CF₃ | H | H | —i-C₃H₇ | 1.5240 |
| 141 | —CHCl₂ | 2-Cl | 4-CH₃ | H | H | —C₂H₅ | 1.5421 |
| 142 | —CHCl₂ | 2-Cl | 4-CH₃ | H | H | —i-C₃H₇ | 1.5428 |
| 143 | —CHCl₂ | 2-Cl | 5-CH₃ | H | H | —C₂H₅ | 1.5568 |
| 144 | —CHCl₂ | 2-Cl | 5-CH₃ | H | H | —i-C₃H₇ | 1.5412 |
| 145 | —CHCl₂ | 2-Cl | 6-CH₃ | H | H | —C₂H₅ | 1.5510 |
| 146 | —CHCl₂ | 2-Cl | 6-CH₃ | H | H | —i-C₃H₇ | 1.5390 |
| 147 | —CHCl₂ | 2-CH₃ | 3-Cl | H | H | —C₂H₅ | 1.5563 |
| 148 | —CHCl₂ | 2-CH₃ | 3-Cl | H | H | —i-C₃H₇ | 1.5440 |
| 149 | —CHCl₂ | 3-Cl | 4-CH₃ | H | H | —C₂H₅ | 1.5600 |
| 150 | —CHCl₂ | 3-Cl | 4-CH₃ | H | H | —i-C₃H₇ | 1.5610 |
| 151 | —CHCl₂ | 2-CH₃ | 4-Cl | H | H | —C₂H₅ | 1.5534 |
| 152 | —CHCl₂ | 2-CH₃ | 4-Cl | H | H | —i-C₃H₇ | 1.5438 |
| 153 | —CHCl₂ | 2-CH₃ | 5-Cl | H | H | —C₂H₅ | 1.5513 |
| 154 | —CHCl₂ | 2-CH₃ | 5-Cl | H | H | —i-C₃H₇ | m.p. 90–93° C. |
| 155 | —CHCl₂ | 2-CH₃ | H | H | H | —i-C₃H₇ | 1.5306 |
| 156 | —CHCl₂ | 2-Cl | 5-Cl | H | H | —C₂H₅ | 1.5610 |
| 157 | —CHCl₂ | 2-Cl | 5-Cl | H | H | —i-C₃H₇ | 1.5487 |
| 158 | —CHCl₂ | 3-CH₃ | H | H | H | —C₂H₅ | 1.5428 |
| 159 | —CHCl₂ | 3-CH₃ | H | H | H | —i-C₃H₇ | 1.5274 |
| 160 | —CHCl₂ | 2-CH₃ | 3-CH₃ | H | H | —C₂H₅ | 1.5528 |
| 161 | —CHCl₂ | 2-CH₃ | 3-CH₃ | H | H | —i-C₃H₇ | 1.5403 |
| 162 | —CHCl₂ | 3-CH₃ | 4-CH₃ | H | H | —C₂H₅ | 1.5595 |
| 163 | —CHCl₂ | 3-CH₃ | 4-CH₃ | H | H | —i-C₃H₇ | 1.5438 |
| 164 | —CHCl₂ | 2-CH₃ | 5-CH₃ | H | H | —C₂H₅ | 1.5480 |

TABLE I-continued

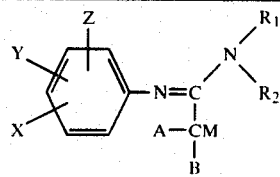

| Compound Number | —CMAB | X | Y | Z | R₁ | R₂ | m.p. °C. or $n_D^{30}$ |
|---|---|---|---|---|---|---|---|
| 165 | —CHCl₂ | 2-CH₃ | 5-CH₃ | H | H | —i-C₃H₇ | 1.5343 |
| 166 | —CHCl₂ | 2-OCH₃ | 5-OCH₃ | H | H | —C₂H₅ | 1.5593 |
| 167 | —CHCl₂ | 2-OCH₃ | 5-OCH₃ | H | H | —i-C₃H₇ | 1.5506 |
| 168 | —CHCl₂ | 2-Cl | 4-Cl | 6-Cl | H | —C₂H₅ | m.p. 71–74° C. |
| 169 | —CHCl₂ | 2-Cl | 4-Cl | 6-Cl | H | —i-C₃H₇ | 1.5743 |
| 170 | —CHCl₂ | 2-CH₃ | 4-CH₃ | H | H | —i-C₃H₇ | 1.5473 |
| 171 | —CHCl₂ | 2-CH₃ | 4-CH₃ | H | H | —C₂H₅ | 1.5473 |
| 172 | —CHCl₂ | 2-CH₃ | 5-NO₂ | H | H | —C₂H₅ | m.p. 96–100° C. |
| 173 | —CHCl₂ | 2-OCH₃ | 5-NO₂ | H | H | —i-C₃H₇ | m.p. 74–78° C. |
| 174 | —CHCl₂ | 3-C(O)CH₃ | H | H | H | —i-C₃H₇ | 1.5590 |
| 175 | —CHCl₂ | 2-Cl | H | H | H | —i-C₃H₇ | 1.5560 |
| 176 | —CHCl₂ | 3-Br | H | H | H | —i-C₃H₇ | 1.5688 |
| 177 | —CHCl₂ | 2-Br | H | H | H | —i-C₃H₇ | 1.5655 |
| 178 | —CHCl₂ | 4-Br | H | H | H | —i-C₃H₇ | 1.5679 |
| 179 | —CHCl₂ | 3-CH₃O | H | H | H | —i-C₃H₇ | 1.5463 |
| 180 | —CHCl₂ | 3-(CH₃)₂NC(O)NH | H | H | H | —i-C₃H₇ | 1.5523 |
| 181 | —CHCl₂ | 3-CH₃ | 5-CH₃ | H | CH(CH₃)₂ | —C(O)—CH₃ | Dark oil |
| 182 | —CHClF | 3-CH₃ | 5-CH₃ | H | H | —i-C₃H₇ | m.p. 37–40° C. |
| 183 | —CHClF | 2-Cl | 3-Cl | H | H | —i-C₃H₇ | Dark oil |
| 184 | —CHClF | 3-Cl | 5-Cl | H | H | —i-C₃H₇ | 1.5540 |
| 185 | —CHCl₂ | 2-OCH₃ | 4-OCH₃ | 5-Cl | H | —i-C₃H₇ | 1.5545 |
| 186 | —CHCl₂ | 2-NO₂ | 4-Cl | H | H | —i-C₃H₇ | 1.5786 |
| 187 | —CHCl₂ | 3-NO₂ | 4-Cl | H | H | —i-C₃H₇ | m.p. 83–86° C. |
| 188 | —CHCl₂ | 3-NO₂ | 6-Cl | H | H | —i-C₃H₇ | m.p. 60–63° C. |
| 189 | —CHCl₂ | 2-Cl | 4-NO₂ | H | H | —i-C₃H₇ | m.p. 84–88° C. |
| 190 | —CHCl₂ | 2-CH₃ | 5-NO₂ | H | H | —i-C₃H₇ | m.p. 54–58° C. |
| 191 | —CHCl₂ | 2-NO₂ | 4-CH₃ | H | H | —i-C₃H₇ | 1.5688 |
| 192 | —CHCl₂ | 3-NO₂ | 4-CH₃ | H | H | —i-C₃H₇ | 1.5677 |
| 193 | —CHCl₂ | 2-F | H | H | H | —i-C₃H₇ | 1.5352 |
| 194 | —CHCl₂ | 2-OCH₃ | 4-NO₂ | H | H | —i-C₃H₇ | 1.5980 |
| 195 | —CHCl₂ | 2-F | 4-F | H | H | —i-C₃H₇ | 1.5173 |
| 196 | —CHCl₂ | 2-i-C₃H₇ | 6-i-C₃H₇ | H | H | —i-C₃H₇ | m.p. 80–82° C. |
| 197 | —CHCl₂ | 3-NO₂ | 4-F | H | H | —i-C₃H₇ | m.p. 88.5–91° C. |
| 198 | —CHCl₂ | 3-Cl | 5-Cl | H | H | —c-C₃H₇ | Low melting solid |
| 199 | —CHCl₂ | 2-Cl | 3-Cl | H | —CH₂CH=CH₂ | —CH₂CH=CH₂ | 1.5860 |
| 200 | —CHCl₂ | 3-CH₃ | 5-CH₃ | H | —CH₂CH=CH₂ | —CH₂CH=CH₂ | 1.5610 |
| 201 | —CHCl₂ | 2-CH₃ | 3-Cl | H | —CH₂CH=CH₂ | —CH₂CH=CH₂ | 1.5744 |
| 202 | —CHCl₂ | 2-CH₃ | 3-Cl | H | —CH₂CH=CH₂ | —CH₂CH=CH₂ | 1.5787 |
| 203 | —CHCl₂ | 2-Cl | 3-Cl | H | H | —CH₂CH=CH₂ | 1.5924 |
| 204 | —CHCl₂ | 3-CH₃ | 5-CH₃ | H | H | —CH₂CH=CH₂ | 1.5629 |
| 205 | —CHCl₂ | 2-CH₃ | 3-Cl | H | H | —n-C₃H₇ | 1.5648 |
| 206 | —CHCl₂ | 2-Cl | 3-Cl | H | H | —n-C₃H₇ | 1.5784 |
| 207 | —CHCl₂ | 3-CH₃ | 5-CH₃ | H | H | —n-C₃H₇ | 1.5505 |
| 208 | —CHBrF | 3-Cl | 5-Cl | H | H | —i-C₃H₇ | Dark oil |
| 209 | —CHCl₂ | 2-Cl | 5-Cl | H | H | —CH₂CH=CH₂ | 1.5897 |
| 210 | —CHF₂ | 3-Cl | 5-Cl | H | H | —i-C₃H₇ | 1.5425 |
| 211 | —CHCl₂ | 2-Cl | 4-Cl | 5-Cl | —CH₃ | —CH₃ | 1.5882 |

TABLE I-A

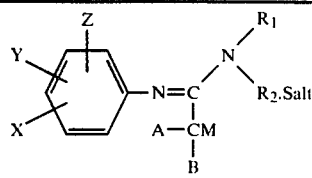

| Compound Number | —CMAB | X | Y | Z | R₁ | R₂ | Acid Salt | m.p. °C. or n_D³⁰ |
|---|---|---|---|---|---|---|---|---|
| 212 | —CHCl₂ | 3-CF₃ | H | H | H | —i-C₄H₉ | HCl | m.p. 127–128° C. |
| 213 | —CHCl₂ | 3-CF₃ | 4-Cl | H | H | —C₃H₇ | HCl | m.p. 139–141° C. |
| 214 | —CHCl₂ | 3-CF₃ | 4-Cl | H | H | —i-C₃H₇ | HCl | m.p. 169–172° C. |
| 215 | —CHCl₂ | 3-CF₃ | 4-Cl | H | H | —CH₂CH=CH₂ | HCl | m.p. 115–120° C. |
| 216 | —CHCl₂ | 3-CF₃ | 4-Cl | H | H | —i-C₃H₇ | CCl₃COOH | 1.4863 |
| 217 | —CHCl₂ | 3-CF₃ | H | H | H | —i-C₃H₇ | HCl | m.p. 191–194° C. |
| 218 | —CHCl₂ | 3-CF₃ | 5-CF₃ | H | H | —C₂H₅ | HCl | m.p. 195–197° C. |
| 219 | —CHCl₂ | 3-NO₂ | H | H | H | —i-C₃H₇ | HCl | m.p. 165–167° C. |
| 220 | —CHCl₂ | 3-Cl | 4-Cl | H | H | —i-C₃H₇ | HCl | m.p. 202–204° C. |
| 221 | —CHCl₂ | 3-Cl | 5-Cl | H | H | —i-C₃H₇ | HCl | m.p. 198–202° C. |
| 222 | —CHCl₂ | 2-Cl | 5-CF₃ | H | H | —C₂H₅ | HCl | m.p. 185–188° C. |
| 223 | —CHCl₂ | 2-Cl | 5-CF₃ | H | H | —i-C₃H₇ | HCl | m.p. 178–179° C. |
| 224 | —CHCl₂ | 2-CF₃ | 4-Cl | H | H | —C₂H₅ | HCl | m.p. 149–150° C. |
| 225 | —CHCl₂ | 2-CF₃ | 4-Cl | H | H | —i-C₃H₇ | HCl | (Foam) |
| 226 | —CHCl₂ | 3-NO₂ | 4-Cl | H | H | —C₂H₅ | HCl | m.p. 148–150° C. |
| 227 | —CHCl₂ | 3-NO₂ | 4-Cl | H | H | —i-C₃H₇ | HCl | m.p. 137–140° C. |
| 228 | —CHCl₂ | 3-SCF₃ | H | H | H | —C₂H₅ | HCl | m.p. 136–138° C. |
| 229 | —CHCl₂ | 3-SCF₃ | H | H | H | —i-C₃H₇ | HCl | m.p. 147–150° C. |
| 230 | —CHCl₂ | 2-CF₃ | H | H | H | —C₂H₅ | HCl | 1.5140 |
| 231 | —CHCl₂ | 2-CF₃ | H | H | H | —i-C₃H₇ | HCl | m.p. 159–161° C. |
| 232 | —CHCl₂ | 3-CH₃ | 5-CH₃ | H | H | —C₂H₅ | HCl | m.p. 152–154° C. |
| 233 | —CHCl₂ | 3-CH₃ | 5-CH₃ | H | H | —i-C₃H₇ | HCl | m.p. 194–197° C. |
| 234 | —CHCl₂ | 2-Cl | 3-Cl | H | H | —C₂H₅ | HCl | m.p. 176–180° C. |
| 235 | —CHCl₂ | 2-Cl | 3-Cl | H | H | —i-C₃H₇ | HCl | m.p. 199–203° C. |
| 236 | —CHCl₂ | 2-Cl | 4-Cl | H | H | —C₂H₅ | HCl | m.p. 125–129° C. |
| 237 | —CHCl₂ | 2-Cl | 4-Cl | H | H | —i-C₃H₇ | HCl | m.p. 159–161° C. |
| 238 | —CHCl₂ | 2-Cl | 6-Cl | H | H | —C₂H₅ | HCl | m.p. 177–181° C. |
| 239 | —CHCl₂ | 2-Cl | 6-Cl | H | H | —i-C₃H₇ | HCl | m.p. 195–198° C. |
| 240 | —CHCl₂ | 3-CN | H | H | H | —C₂H₅ | HCl | m.p. 136–140° C. |
| 241 | —CHCl₂ | 3-CN | H | H | H | —i-C₃H₇ | HCl | m.p. 167–169° C. |
| 242 | —CHCl₂ | 2-CH₃ | 6-CH₃ | H | H | —C₂H₅ | HCl | m.p. 183–186° C. |
| 243 | —CHCl₂ | 2-CH₃ | 6-CH₃ | H | H | —i-C₃H₇ | HCl | m.p. 198–202° C. |
| 244 | —CHCl₂ | 2-C₂H₅ | 6-C₂H₅ | H | H | —C₂H₅ | HCl | m.p. 175–179° C. |
| 245 | —CHCl₂ | 2-C₂H₅ | 6-C₂H₅ | H | H | —i-C₃H₇ | HCl | m.p. 195–198° C. |
| 246 | —CHCl₂ | 3-NO₂ | 5-NO₂ | H | H | —C₂H₅ | HCl | m.p. 201–202° C. |
| 247 | —CHCl₂ | 3-NO₂ | 5-NO₂ | H | H | —i-C₃H₇ | HCl | m.p. 197–202° C. |
| 248 | —CHCl₂ | 2-NO₂ | 4-CF₃ | H | H | —C₂H₅ | HCl | Glass |
| 249 | —CHCl₂ | 2-NO₂ | 4-CF₃ | H | H | —i-C₃H₇ | HCl | m.p. 152–155° C. |
| 250 | —CHCl₂ | 2-Cl | 4-CH₃ | H | H | —C₂H₅ | HCl | m.p. 160–163° C. |
| 251 | —CHCl₂ | 2-Cl | 4-CH₃ | H | H | —i-C₃H₇ | HCl | m.p. 183–184° C. |
| 252 | —CHCl₂ | 2-Cl | 5-CH₃ | H | H | —C₂H₅ | HCl | m.p. 184–185° C. |
| 253 | —CHCl₂ | 2-Cl | 5-CH₃ | H | H | —i-C₃H₇ | HCl | m.p. 206–207° C. |
| 254 | —CHCl₂ | 2-Cl | 6-CH₃ | H | H | —C₂H₅ | HCl | m.p. 166–168° C. |
| 255 | —CHCl₂ | 2-Cl | 6-CH₃ | H | H | —i-C₃H₇ | HCl | m.p. 185–187° C. |
| 256 | —CHCl₂ | 2-CH₃ | 3-Cl | H | H | —C₂H₅ | HCl | m.p. 188–191° C. |
| 257 | —CHCl₂ | 2-CH₃ | 3-Cl | H | H | —i-C₃H₇ | HCl | m.p. 236° C. dec. |
| 258 | —CHCl₂ | 3-Cl | 4-CH₃ | H | H | —C₂H₅ | HCl | m.p. 166–169° C. |
| 259 | —CHCl₂ | 3-Cl | 4-CH₃ | H | H | —i-C₃H₇ | HCl | m.p. 183–186° C. |
| 260 | —CHCl₂ | 2-CH₃ | 4-Cl | H | H | —C₂H₅ | HCl | m.p. 184–186° C. |
| 261 | —CHCl₂ | 2-CH₃ | 4-Cl | H | H | —i-C₃H₇ | HCl | m.p. 193–195° C. |
| 262 | —CHCl₂ | 2-CH₃ | 5-Cl | H | H | —C₂H₅ | HCl | m.p. 165–166° C. |
| 263 | —CHCl₂ | 2-CH₃ | 5-Cl | H | H | —i-C₃H₇ | HCl | m.p. 211–213° C. |
| 264 | —CHCl₂ | 2-CH₃ | H | H | H | —i-C₃H₇ | HCl | m.p. 223–224° C. dec. |
| 265 | —CHCl₂ | 3-CF₃ | 5-CF₃ | H | H | —i-C₃H₇ | HCl | m.p. 158–160° C. |
| 266 | —CHCl₂ | 2-Cl | 5-Cl | H | H | —C₂H₅ | HCl | m.p. 183–184° C. |
| 267 | —CHCl₂ | 2-Cl | 5-Cl | H | H | —i-C₃H₇ | HCl | m.p. 196–199° C. |
| 268 | —CHCl₂ | 3-CH₃ | H | H | H | —C₂H₅ | HCl | m.p. 134–136° C. |
| 269 | —CHCl₂ | 3-CH₃ | H | H | H | —i-C₃H₇ | HCl | m.p. 212–215° C. |
| 270 | —CHCl₂ | 2-CH₃ | 3-CH₃ | H | H | —C₂H₅ | HCl | m.p. 187–189° C. |
| 271 | —CHCl₂ | 2-CH₃ | 3-CH₃ | H | H | —i-C₃H₇ | HCl | m.p. 243–244° C. |
| 272 | —CHCl₂ | 3-CH₃ | 4-CH₃ | H | H | —C₂H₅ | HCl | m.p. 140–142° C. |
| 273 | —CHCl₂ | 3-CH₃ | 4-CH₃ | H | H | —i-C₃H₇ | HCl | m.p. 213–219° C. |
| 274 | —CHCl₂ | 2-CH₃ | 5-CH₃ | H | H | —C₂H₅ | HCl | m.p. 134–137° C. |
| 275 | —CHCl₂ | 2-CH₃ | 5-CH₃ | H | H | —i-C₃H₇ | HCl | m.p. 230–231° C. |
| 276 | —CHCl₂ | 2-OCH₃ | 5-OCH₃ | H | H | —C₂H₅ | HCl | m.p. 146–149° C. |
| 277 | —CHCl₂ | 2-Cl | 4-Cl | 6-Cl | H | —C₂H₅ | HCl | m.p. 194° C. dec. |
| 278 | —CHCl₂ | 2-Cl | 4-Cl | 6-Cl | H | —i-C₃H₇ | HCl | m.p. 188° C. dec. |
| 279 | —CHCl₂ | 2-CH₃ | 4-CH₃ | H | H | —i-C₃H₇ | HCl | m.p. 186–188° C. |
| 280 | —CHCl₂ | 2-CH₃ | 4-CH₃ | H | H | —C₂H₅ | HCl | m.p. 161–165° C. |
| 281 | —CHCl₂ | 2-CH₃ | 5-NO₂ | H | H | —C₂H₅ | HCl | m.p. 165–168° C. |
| 282 | —CHCl₂ | 2-OCH₃ | 5-NO₂ | H | H | —i-C₃H₇ | HCl | m.p. 129–131° C. dec. |

TABLE I-A-continued $$\begin{array}{c} Z \\ Y \diagdown \diagup \diagdown \diagup R_1 \\ \diagup \diagdown N = C \diagdown N \\ X \diagup \diagdown \diagup \quad | \quad R_2 \cdot Salt \\ A - CM \\ | \\ B \end{array}$$

| Compound Number | —CMAB | X | Y | Z | $R_1$ | $R_2$ | Acid Salt | m.p. °C. or $n_D^{30}$ |
|---|---|---|---|---|---|---|---|---|
| 283 | —CHCl$_2$ | 3-CH$_3$ | 5-CH$_3$ | H | H | —i-C$_3$H$_7$ | 2,4-dichloro phenoxy acetic acid | Very viscous oil |
| 284 | —CHCl$_2$ | 3-CH$_3$ | 5-CH$_3$ | H | H | —i-C$_3$H$_7$ | Dichloro benzoic acid | Semi-solid |
| 285 | —CHCl$_2$ | 3-Cl | 5-Cl | H | H | —i-C$_3$H$_7$ | Hexanoic acid salt | 1.5150 |
| 286 | —CHCl$_2$ | 3-Cl | 5-Cl | H | H | —i-C$_3$H$_7$ | Naphthalene acetic acid | m.p. 131° C. |
| 287 | —CHCl$_2$ | 3-Cl | 5-Cl | H | H | —i-C$_3$H$_7$ | Trifluoroacetic acid | Semi-solid |
| 288 | —CHCl$_2$ | 3-Cl | 5-Cl | H | H | —i-C$_3$H$_7$ | Pivalic acid | $n_D^{30}$ 1.5192 |
| 289 | —CHCl$_2$ | 3-Cl | 5-Cl | H | H | —i-C$_3$H$_7$ | Stearic acid | Semi-solid |
| 290 | —CHCl$_2$ | 3-Cl | 5-Cl | H | H | —i-C$_3$H$_7$ | 10-undecenoic acid | $n_D^{30}$ 1.5163 |
| 291 | —CHCl$_2$ | 3-Cl | 5-Cl | H | H | —i-C$_3$H$_7$ | Benzoic acid | Semi-solid |
| 292 | —CHCl$_2$ | 3-Cl | 5-Cl | H | H | —i-C$_3$H$_7$ | Melonic acid | Semi-solid |
| 293 | —CHCl$_2$ | 3-Cl | 5-Cl | H | H | —i-C$_3$H$_7$ | Succinic acid | Semi-solid |
| 294 | —CHCl$_2$ | 3-Cl | 5-Cl | H | H | —i-C$_3$H$_7$ | Maleic acid | $n_D^{30}$ 1.5523 |

HERBICIDE SCREENING TESTS

As previously mentioned, the herein described compounds produced in the above-described manner are phytotoxic compounds which are useful and valuable in conrolling various plant species. Compounds of this invention were tested as herbicides in the following manner.

A. Pre-emergence Herbicide Screening Test

Using an analytical balance, 300 milligrams of the compound to be tested is weighed on a piece of glassine weighing paper. The paper and compound are placed in a 2 oz. amber bottle and dissolve in 45 milliliters of acetone. If the material is not soluble in acetone, another solvent such as water, alcohol, or dimethylformamide (DMF) is used. When DMF is used, only 1.5 milliliters o less are used to dissolve the compound and then another solvent is used to bring the volume to 45 milliliters. Twenty milliliters of this solution is transferred to a 80 milliliter wide-mouth amber bottle and diluted with 24.5 milliliters of a water and acetone mixture (10:1) containing 1% Tween 20 ® (polyoxyethylene sorbitan monolaurate). The solution is sprayed on the seeded flat on a linear spray table calibrated to deliver 80 gallon per acre, the application rate is 2 lb/acre (2.24 kg/hectare).

When applied at 8 lb/acre (8.96 kg/hectare), 20 milligrams of the compound to be tested are weighed onto a glassine weighing paper, placed into a 30 milliliter vial, and dissolved in 3 milliliters acetone containing 1% Tween 20 ® . If the material is not soluble in acetone, another solvent such as water, alcohol, or dimethylformamide (DMF) is used. When DMF is used, only 0.5 milliliters or less are used to dissolve the compound and then another solvent is used to bring the volume to 3 milliliters. The solution is atomized onto the seeded flat using a No. 152 DeVilbiss atomizer at a pressure of 5 lb/square inch (0.35 kg/cm$^2$), and the spray volume was 143 gallons per acre (1338 liter per hectare).

On the day preceeding treatment, a flat is filled with sandy loam soil fortified with 50 ppm 17-17-17 fertilizer and Captan ®. Seven rows are impressed across the width of the flat and seeded with one species per row. The seeds are covered with soil so that they are planted at a depth of 1.2 centimeters. The species are hairy crabgrass (CG) (*Digitaria sanguinalis*), foxtail (FT) (*Setaria spp.*), watergrass (WG) (*Echinochloa crusgali*), wild oat (WO) (*Avena fatua*), mustard (MD) (*Brassica juncea*), curly dock (CD) (*Rumex crispus*), and pigweed (PW) (*Amaranthus retroflexus*) is seeded between the last row and the end of the flat at a depth of 1 centimeter. Ample seeds are planted to give about 20 to 50 seedlings per row after emergence depending on the size of the plant at the time of rating. At the 8 lb/acre testing rate red oat (RO) (*Avena sativa*) is used instead of wild oat.

After treatment, the flats are placed in the greenhouse at a temperature of 70° to 85° F. and water by sprinkling. Two weeks after treatment the degree of injury or control is determined by comparison with untreated plants of the same age. The injury rating is recorded as 0 to 100% for each species where 0 represents no injury and 100% represents complete kill.

B. Post-emergence Herbicide Screening Test

The procedure for this test is substantially the same as the pre-emergence herbicide screening test A. The seeds of the plant species for the 2 lb/acre test are described in screening test A. The seeds for the 8 lb/acre post-emergence test included: hairy crabgrass, watergrass, red oat, mustard, curly dock and pinto beans (BN) (*Phaseolus vulgaris*). The flats are seeded and placed in the greenhouse 8–12 days prior to treatment with the candidate compounds. The plant foliage was sprayed with solutions of the candidate compounds.

For the 8 lb/acre solution, 20 milligrams of the test compound was weighed out and dissolved as described above except that 2.5 milliliters acetone with 1% Tween 20 ® or other suitable solvent plus 2.5 milligrams of water was atomized as described above. The spray volume as 238 gallons per acre (2226 liters per hectare). The rate at 2 lb/acre (2.24 kg/hectare) was achieved using the linear spray table as described above.

The results of these tests are shown in Table II.

TABLE II

Herbicidal Activity - Screening Results

Percent Control at 8 lb/A

TABLE II-continued

Herbicidal Activity - Screening Results

| Compound Number | Pre-emergence | | | | | | | Post-emergence | | | | | |
|---|---|---|---|---|---|---|---|---|---|---|---|---|---|
| | CG | FT | WG | RO | PW | MD | CD | CG | WG | RO | MD | CD | BN |
| 1 | 90 | 80 | 80 | 0 | 0 | 0 | 0 | 0 | 0 | 0 | 0 | 0 | 0 |
| 2 | 90 | 80 | 80 | 70 | 0 | 0 | 0 | 0 | 0 | 0 | 0 | 0 | 0 |
| 3 | 0 | 0 | 0 | 0 | 0 | 0 | 0 | 80 | 70 | 0 | 100 | 80 | 40 |
| 4 | 0 | 0 | 0 | 0 | 0 | 0 | 0 | 0 | 0 | 0 | 100 | 0 | 0 |
| 5 | 100 | 80 | 80 | 60 | 0 | 0 | 0 | 80 | 70 | 70 | 0 | 0 | 0 |
| 6 | 80 | 80 | 80 | 60 | 100 | 30 | 20 | 0 | 0 | 0 | 0 | 0 | 0 |
| 7 | 40 | 40 | 0 | 0 | 0 | 0 | 0 | 0 | 0 | 0 | 100 | 0 | 0 |
| 8 | 0 | 0 | 0 | 0 | 0 | 0 | 0 | 20 | 0 | 0 | 0 | 0 | 10 |
| 9 | 0 | 0 | 0 | 0 | 0 | 0 | 0 | 0 | 0 | 0 | 30 | 0 | 20 |
| 10 | 0 | 0 | 0 | 0 | 0 | 0 | 0 | 0 | 0 | 0 | 80 | 0 | 0 |
| 11 | 0 | 0 | 0 | 0 | 0 | 30 | 0 | 100 | 95 | 30 | 100 | 80 | 40 |
| 12 | 0 | 0 | 0 | 0 | 0 | 0 | 0 | 95 | 20 | 10 | 0 | 0 | 0 |
| 13 | 100 | 99 | 99 | 90 | 45 | 20 | 45 | 95 | 95 | 0 | 0 | 20 | 0 |
| 14 | 99 | 96 | 95 | 30 | 0 | 0 | 35 | 95 | 95 | 0 | 0 | 20 | 0 |
| 15 | 99 | 98 | 98 | 99 | 0 | 0 | 65 | 98 | 95 | 10 | 0 | 20 | 0 |
| 16 | 80 | 80 | 90 | 20 | 0 | 0 | 0 | 0 | 0 | 0 | 0 | 0 | 0 |
| 17 | 98 | 98 | 98 | 60 | 40 | 20 | 90 | 95 | 95 | 0 | 0 | 20 | 10 |
| 18 | 95 | 95 | 90 | 95 | 0 | 0 | 85 | 95 | 95 | 0 | 0 | 20 | 10 |
| 19 | 80 | 80 | 60 | 10 | 0 | 0 | 0 | 95 | 95 | 0 | 0 | 0 | 0 |
| 20 | 80 | 80 | 80 | 0 | 35 | 20 | 40 | 95 | 60 | 0 | 20 | 20 | 10 |
| 21 | 0 | 0 | 0 | 0 | 0 | 0 | 0 | 0 | 0 | 0 | 10 | 0 | 0 |
| 22 | 0 | 0 | 0 | 0 | 0 | 0 | 0 | 0 | 0 | 0 | 10 | 0 | 0 |
| 23 | 0 | 0 | 0 | 0 | 0 | 0 | 0 | 0 | 0 | 0 | 50 | 0 | 0 |
| 24 | 98 | 40 | 40 | 0 | 20 | 10 | 20 | 95 | 80 | 0 | 0 | 30 | 10 |
| 25 | 0 | 0 | 0 | 0 | 0 | 0 | 0 | 0 | 0 | 0 | 0 | 0 | 10 |
| 26 | 0 | 0 | 0 | 98 | 60 | 0 | 0 | 0 | 0 | 0 | 0 | 0 | 0 |
| 27 | 0 | 0 | 0 | 0 | 0 | 0 | 0 | 0 | 0 | 0 | 0 | 0 | 70 |
| 28 | 0 | 0 | 0 | 0 | 80 | 60 | 60 | 20 | 0 | 0 | 20 | 0 | 0 |
| 29 | 0 | 0 | 0 | 0 | 0 | 95 | 0 | 0 | 0 | 0 | 0 | 0 | 40 |
| 30 | 0 | 0 | 0 | 0 | 80 | 60 | 0 | 0 | 0 | 0 | 0 | 0 | 0 |
| 31 | 0 | 0 | 0 | 0 | 98 | 30 | 40 | 0 | 0 | 0 | 0 | 0 | 0 |
| 32 | 0 | 0 | 0 | 0 | 0 | 0 | 0 | 40 | 40 | 0 | 0 | 0 | 0 |
| 33 | 95 | 90 | 80 | 0 | 50 | 90 | 0 | 0 | 0 | 0 | 0 | 0 | 0 |
| 34 | 40 | 90 | 0 | 0 | 0 | 20 | 0 | 0 | 0 | 0 | 0 | 0 | 0 |
| 35 | 0 | 0 | 0 | 0 | 0 | 0 | 0 | 100 | 60 | 20 | 0 | 0 | 0 |
| 36 | 0 | 0 | 0 | 0 | 0 | 0 | 0 | 90 | 50 | 20 | 70 | 0 | 60 |
| 37 | 95 | 30 | 20 | 0 | 0 | 0 | 0 | 0 | 0 | 0 | 0 | 0 | 0 |
| 38 | 0 | 0 | 0 | 0 | 95 | 60 | 50 | 0 | 0 | 0 | 0 | 0 | 0 |
| 39 | 98 | 95 | 80 | 0 | 20 | 40 | 30 | 30 | 30 | 0 | 30 | 0 | 60 |
| 40 | 0 | 0 | 0 | 0 | 80 | 20 | 0 | 0 | 0 | 0 | 0 | 0 | 0 |
| 41 | 98 | 98 | 80 | 0 | 60 | 20 | 30 | 0 | 0 | 0 | 0 | 0 | 0 |
| 42 | 0 | 0 | 20 | 10 | 100 | 30 | 20 | 0 | 0 | 0 | 0 | 0 | 0 |
| 43 | 100 | 99 | 98 | 0 | 97 | 70 | 90 | 100 | 95 | 30 | 100 | 40 | 40 |
| 44 | 98 | 99 | 98 | 30 | 97 | 50 | 95 | 95 | 90 | 30 | 98 | 50 | 20 |
| 45 | 98 | 99 | 95 | 80 | 70 | 0 | 40 | 95 | 80 | 50 | 90 | 50 | 40 |
| 46 | 100 | 99 | 98 | 60 | 98 | 40 | 95 | 95 | 80 | 30 | 40 | 40 | 50 |
| 47 | 99 | 99 | 97 | 30 | 95 | 30 | 95 | 95 | 90 | 40 | 90 | 60 | 50 |
| 48 | 99 | 99 | 80 | 0 | 40 | 0 | 20 | 95 | 80 | 30 | 50 | 40 | 40 |
| 49 | 100 | 99 | 98 | 10 | 97 | 20 | 70 | 90 | 80 | 30 | 50 | 50 | 50 |
| 50 | 99 | 99 | 98 | 20 | 30 | 0 | 20 | 95 | 80 | 60 | 70 | 60 | 10 |
| 51 | 99 | 98 | 60 | 70 | 0 | 0 | 30 | 98 | 80 | 20 | 30 | 40 | 0 |
| 52 | 98 | 98 | 50 | 30 | 50 | 20 | 60 | 98 | 80 | 40 | 40 | 40 | 50 |
| 53 | 100 | 100 | 98 | 20 | 60 | 40 | 80 | 98 | 80 | 40 | 40 | 50 | 50 |
| 54 | 30 | 0 | 0 | 0 | 0 | 0 | 0 | 0 | 0 | 0 | 0 | 0 | 0 |
| 55 | 90 | 30 | 30 | 0 | 95 | 0 | 0 | 0 | 0 | 0 | 0 | 0 | 0 |
| 56 | 20 | 10 | 20 | 0 | 0 | 0 | 0 | 0 | 0 | 0 | 0 | 0 | 0 |
| 57 | 98 | 98 | 98 | 80 | 80 | 0 | 30 | 98 | 70 | 30 | 0 | 0 | 40 |
| 58 | 100 | 98 | 98 | 0 | 80 | 20 | 70 | 95 | 95 | 30 | 30 | 20 | 0 |
| 59 | 0 | 0 | 0 | 0 | 0 | 0 | 0 | 95 | 80 | 0 | 0 | 0 | 0 |
| 60 | 98 | 95 | 95 | 0 | 0 | 0 | 0 | 40 | 20 | 0 | 0 | 0 | 30 |
| 61 | 99 | 98 | 80 | 80 | 80 | 20 | 60 | 98 | 95 | 95 | 0 | 0 | 30 |
| 62 | 97 | 95 | 95 | 0 | 0 | 0 | 0 | 98 | 80 | 0 | 100 | 40 | 10 |
| 63 | 100 | 100 | 100 | 100 | 80 | 20 | 100 | 0 | 0 | 0 | 0 | 0 | 0 |
| 64 | 100 | 100 | 100 | 95 | 80 | 10 | 80 | 0 | 0 | 0 | 0 | 0 | 20 |
| 65 | 100 | 100 | 100 | 97 | 50 | 20 | 95 | 0 | 0 | 0 | 0 | 0 | 20 |
| 66 | 100 | 100 | 100 | 99 | 98 | 70 | 98 | 20 | 0 | 30 | 0 | 0 | 20 |
| 67 | 100 | 99 | 99 | 0 | 0 | 0 | 0 | 0 | 0 | 0 | 0 | 0 | 0 |
| 68 | 100 | 100 | 99 | 98 | 30 | 30 | 90 | 0 | 0 | 0 | 0 | 0 | 0 |
| 69 | 100 | 100 | 99 | 95 | 80 | 0 | 98 | 0 | 0 | 0 | 0 | 0 | 0 |
| 70 | 100 | 100 | 99 | 20 | 30 | 20 | 40 | 40 | 0 | 0 | 10 | 0 | 20 |
| 71 | 100 | 100 | 99 | 0 | 0 | 20 | 30 | 0 | 0 | 0 | 20 | 30 | 30 |
| 72 | 100 | 95 | 90 | 30 | 0 | 0 | 0 | 0 | 0 | 0 | 0 | 0 | 0 |
| 73 | 100 | 90 | 95 | 40 | 0 | 0 | 0 | 0 | 0 | 0 | 0 | 0 | 0 |
| 74 | 100 | 98 | 98 | 10 | 20 | 0 | 0 | 90 | 40 | 20 | 20 | 0 | 30 |
| 75 | 100 | 100 | 100 | 50 | 99 | 50 | 80 | 98 | 98 | 20 | 20 | 30 | 40 |
| 76 | 100 | 100 | 100 | 20 | 95 | 20 | 0 | 98 | 90 | 0 | 0 | 20 | 10 |
| 77 | 100 | 99 | 99 | 0 | 80 | 10 | 20 | 90 | 60 | 0 | 0 | 0 | 30 |
| 78 | 100 | 98 | 98 | 0 | 10 | 20 | 0 | 30 | 30 | 0 | 0 | 0 | 20 |

TABLE II-continued

Herbicidal Activity - Screening Results

| | | | | | | | | | | | | | |
|---|---|---|---|---|---|---|---|---|---|---|---|---|---|
| 79 | 100 | 100 | 100 | 20 | 80 | 20 | 90 | 0 | 0 | 0 | 0 | 0 | 10 |
| 80 | 80 | 40 | 95 | 0 | 0 | 0 | 0 | 0 | 0 | 0 | 0 | 0 | 0 |
| 81 | 100 | 100 | 100 | 0 | 98 | 80 | 90 | 95 | 60 | 0 | 10 | 20 | 30 |
| 82 | 100 | 99 | 99 | 0 | 95 | 40 | 70 | 80 | 80 | 0 | 20 | 20 | 40 |
| 83 | 100 | 100 | 100 | 10 | 98 | 40 | 98 | 95 | 80 | 20 | 30 | 40 | 40 |
| 84 | 100 | 100 | 99 | 10 | 80 | 50 | 95 | 95 | 90 | 0 | 20 | 30 | 40 |
| 85 | 0 | 0 | 0 | 0 | 0 | 0 | 0 | 0 | 0 | 0 | 10 | 0 | 0 |
| 86 | 98 | 98 | 80 | 0 | 30 | 0 | 10 | 90 | 70 | 10 | 30 | 20 | 40 |
| 87 | 98 | 98 | 50 | 0 | 0 | 0 | 0 | 95 | 80 | 10 | 30 | 30 | 40 |
| 88 | 100 | 100 | 95 | 0 | 70 | 0 | 20 | 95 | 80 | 0 | 10 | 30 | 40 |
| 89 | 100 | 99 | 95 | 0 | 20 | 0 | 0 | 95 | 10 | 0 | 30 | 30 | 40 |
| 90 | 98 | 20 | 20 | 0 | 0 | 0 | 0 | 60 | 0 | 0 | 70 | 20 | 20 |
| 91 | 100 | 100 | 100 | 90 | 99 | 95 | 95 | 98 | 95 | 60 | 80 | 80 | 80 |
| 92 | 100 | 100 | 100 | 70 | 98 | 90 | 95 | 95 | 80 | 40 | 60 | 80 | 40 |
| 93 | 100 | 100 | 100 | 92 | 98 | 95 | 98 | 98 | 80 | 80 | 95 | 95 | 80 |
| 94 | 100 | 100 | 99 | 20 | 90 | 90 | 98 | 95 | 98 | 90 | 98 | 95 | 80 |
| 95 | 100 | 100 | 99 | 30 | 95 | 80 | 90 | 95 | 80 | 80 | 70 | 80 | 70 |
| 96 | 100 | 100 | 99 | 20 | 95 | 40 | 90 | 95 | 80 | 20 | 40 | 80 | 40 |
| 97 | 100 | 98 | 40 | 0 | 95 | 0 | 0 | 98 | 80 | 20 | 20 | 80 | 30 |
| 98 | 100 | 99 | 99 | 20 | 97 | 10 | 60 | 95 | 60 | 0 | 10 | 80 | 30 |
| 99 | 100 | 98 | 98 | 20 | 60 | 30 | 50 | 95 | 80 | 10 | 40 | 80 | 40 |
| 100 | 100 | 100 | 100 | 80 | 95 | 10 | 80 | 98 | 80 | 0 | 0 | 90 | 40 |
| 101 | 100 | 98 | 99 | 30 | 98 | 10 | 50 | 99 | 70 | 10 | 40 | 80 | 30 |
| 102 | 99 | 99 | 97 | 20 | 98 | 0 | 20 | 98 | 95 | 0 | 30 | 80 | 40 |
| 103 | 99 | 98 | 95 | 60 | 99 | 30 | 70 | 95 | 70 | 20 | 10 | 30 | 40 |
| 104 | 90 | 50 | 40 | 20 | 10 | 0 | 0 | 10 | 0 | 0 | 10 | 0 | 0 |
| 105 | 99 | 30 | 20 | 10 | 98 | 0 | 0 | 0 | 0 | 0 | 10 | 0 | 0 |
| 106 | 100 | 100 | 99 | 20 | 95 | 40 | 50 | 98 | 90 | 40 | 100 | 60 | 30 |
| 107 | 95 | 90 | 80 | 10 | 0 | 0 | 0 | 70 | 0 | 0 | 0 | 30 | 0 |
| 108 | 98 | 97 | 97 | 20 | 98 | 10 | 30 | 99 | 60 | 10 | 20 | 30 | 40 |
| 109 | 0 | 0 | 0 | 0 | 0 | 0 | 0 | 80 | 10 | 0 | 30 | 0 | 0 |
| 110 | 100 | 50 | 80 | 30 | 0 | 0 | 0 | 30 | 0 | 0 | 10 | 0 | 0 |
| 111 | 95 | 40 | 70 | 20 | 95 | 0 | 0 | 0 | 0 | 0 | 20 | 0 | 0 |
| 112 | 98 | 40 | 40 | 0 | 60 | 0 | 0 | 0 | 0 | 0 | 10 | 0 | 0 |
| 113 | 70 | 20 | 20 | 0 | 0 | 10 | 0 | 0 | 0 | 0 | 0 | 0 | 0 |
| 114 | 100 | 99 | 99 | 97 | 40 | 0 | 70 | 98 | 90 | 10 | 0 | 60 | 40 |
| 115 | 100 | 99 | 99 | 40 | 30 | 20 | 80 | 98 | 95 | 80 | 0 | 100 | 40 |
| 116 | 99 | 98 | 98 | 70 | 20 | 20 | 40 | 98 | 95 | 0 | 10 | 40 | 40 |
| 117 | 100 | 98 | 98 | 60 | 10 | 20 | 10 | 95 | 60 | 10 | 30 | 100 | 50 |
| 118 | 99 | 98 | 95 | 0 | 0 | 0 | 0 | 98 | 30 | 20 | 0 | 0 | 30 |
| 119 | 98 | 98 | 95 | 30 | 0 | 0 | 0 | 98 | 10 | 0 | 0 | 30 | 10 |
| 120 | 99 | 97 | 98 | 30 | 20 | 0 | 10 | 98 | 80 | 20 | 0 | 50 | 40 |
| 121 | 100 | 98 | 97 | 80 | 0 | 0 | 0 | 99 | 98 | 30 | 0 | 98 | 30 |
| 122 | 0 | 0 | 0 | 0 | 0 | 100 | 0 | 0 | 0 | 0 | 100 | 0 | 0 |
| 123 | 30 | 0 | 30 | 30 | 60 | 30 | 40 | 90 | 70 | 10 | 0 | 0 | 0 |
| 124 | 99 | 97 | 98 | 80 | 0 | 0 | 40 | 70 | 30 | 0 | 0 | 0 | 0 |
| 125 | 100 | 100 | 100 | 100 | 98 | 80 | 60 | 98 | 90 | 20 | 30 | 98 | 60 |
| 126 | 100 | 100 | 100 | 99 | 98 | 80 | 95 | 98 | 90 | 30 | 30 | 60 | 60 |
| 127 | — | 100 | 100 | 99 | 99 | 95 | 99 | — | 90 | 0 | 40 | 40 | 40 |
| 128 | — | 100 | 100 | 99 | 98 | 95 | 99 | — | 80 | 10 | 40 | 40 | 40 |
| 129 | — | 100 | 100 | 95 | 98 | 40 | 98 | — | 40 | 0 | 0 | 0 | 10 |
| 130 | — | 100 | 99 | 95 | 80 | 0 | 95 | — | 40 | 0 | 0 | 40 | 30 |
| 131 | — | 95 | 98 | 20 | 80 | 60 | 70 | — | 0 | 0 | 0 | 0 | 10 |
| 132 | — | 100 | 99 | 90 | 30 | 20 | 70 | — | 0 | 0 | 0 | 0 | 20 |
| 133 | — | 90 | 98 | 30 | 0 | 0 | 0 | — | 0 | 0 | 0 | 0 | 0 |
| 134 | — | 100 | 100 | 99 | 95 | 20 | 40 | — | 40 | 10 | 0 | 0 | 30 |
| 135 | — | 0 | 0 | 0 | 0 | 0 | 0 | — | 0 | 0 | 0 | 0 | 10 |
| 136 | — | 98 | 95 | 10 | 0 | 0 | 0 | — | 0 | 0 | 0 | 0 | 0 |
| 137 | — | 40 | 40 | 0 | 0 | 0 | 0 | — | 0 | 0 | 0 | 0 | 0 |
| 138 | — | 95 | 98 | 40 | 80 | 20 | 0 | — | 70 | 0 | 0 | 0 | 0 |
| 139 | — | 96 | 97 | 60 | 0 | 0 | 0 | — | 0 | 0 | 0 | 0 | 0 |
| 140 | — | 99 | 98 | 40 | 0 | 0 | 0 | — | 0 | 0 | 0 | 0 | 0 |
| 141 | — | 98 | 98 | 30 | 80 | 0 | 0 | — | 40 | 0 | 0 | 0 | 20 |
| 142 | — | 100 | 100 | 40 | 30 | 0 | 0 | — | 70 | 0 | 0 | 0 | 0 |
| 143 | — | 100 | 100 | 40 | 30 | 10 | 0 | — | 40 | 0 | 0 | 0 | 20 |
| 144 | — | 100 | 100 | 100 | 98 | 98 | 95 | — | 80 | 0 | 30 | 0 | 30 |
| 145 | — | 100 | 100 | 97 | 95 | 95 | 98 | — | 80 | 0 | 0 | 0 | 40 |
| 146 | — | 80 | 95 | 10 | 0 | 0 | 0 | — | 0 | 0 | 0 | 0 | 0 |
| 147 | — | 30 | 40 | 0 | 0 | 0 | 0 | — | 0 | 0 | 0 | 0 | 0 |
| 148 | — | 100 | 100 | 97 | 98 | 97 | 99 | — | 85 | 20 | 70 | 40 | 20 |
| 149 | — | 100 | 100 | 97 | 98 | 97 | 99 | — | 80 | 0 | 30 | 0 | 70 |
| 150 | — | 100 | 100 | 40 | 40 | 30 | 0 | — | 60 | 0 | 30 | 0 | 0 |
| 151 | — | 100 | 100 | 10 | 0 | 0 | 0 | — | 75 | 0 | 30 | 0 | 50 |
| 152 | — | 100 | 99 | 70 | 20 | 0 | 0 | — | 60 | 0 | 30 | 0 | 0 |
| 153 | — | 100 | 100 | 98 | 40 | 30 | 80 | — | 95 | 0 | 40 | 0 | 60 |
| 154 | — | 100 | 100 | 40 | 10 | 50 | 60 | — | 20 | 0 | 0 | 0 | 30 |
| 155 | — | 100 | 100 | 70 | 90 | 90 | 90 | — | 20 | 0 | 20 | 0 | 20 |
| 156 | — | 0 | 0 | 0 | 0 | 0 | 0 | — | 30 | 0 | 0 | 0 | 20 |
| 157 | — | 100 | 100 | 80 | 80 | 80 | 98 | — | 95 | 40 | 70 | 60 | 30 |
| 158 | — | 100 | 100 | 98 | 98 | 98 | 98 | — | 95 | 0 | 30 | 0 | 50 |
| 159 | — | 40 | 50 | 20 | 0 | 0 | 0 | — | 0 | 0 | 0 | 0 | 0 |

TABLE II-continued

Herbicidal Activity - Screening Results

| | | | | | | | | | | | | | |
|---|---|---|---|---|---|---|---|---|---|---|---|---|---|
| 160 | — | 98 | 100 | 40 | 30 | 10 | 80 | — | 0 | 0 | 0 | 0 | 0 |
| 161 | — | 100 | 100 | 95 | 40 | 50 | 0 | — | 85 | 10 | 70 | 0 | 0 |
| 162 | — | 100 | 100 | 100 | 0 | 80 | 20 | — | 90 | 20 | 0 | 0 | 40 |
| 163 | — | 100 | 100 | 0 | 20 | 20 | 0 | — | 20 | 0 | 0 | 0 | 0 |
| 164 | — | 100 | 100 | 20 | 0 | 0 | 0 | — | 80 | 0 | 20 | 20 | 0 |
| 165 | — | 100 | 100 | 100 | 50 | 70 | 20 | — | 30 | 20 | 10 | 0 | 0 |
| 166 | — | 100 | 100 | 100 | 80 | 80 | 80 | — | 90 | 30 | 0 | 0 | 40 |
| 167 | — | 90 | 70 | 0 | 0 | 0 | 0 | — | 0 | 0 | 0 | 0 | 0 |
| 168 | — | 80 | 70 | 0 | 0 | 0 | 0 | — | 0 | 0 | 0 | 0 | 20 |
| 169 | — | 100 | 98 | 30 | 40 | 0 | 40 | — | 95 | 0 | 30 | 80 | 50 |
| 170 | — | 100 | 99 | 40 | 50 | 30 | 50 | — | 95 | 20 | 20 | 40 | 60 |
| 171 | — | 98 | 98 | 98 | 0 | 0 | 0 | — | 60 | 0 | 0 | 0 | 0 |
| 172 | — | 98 | 98 | 40 | 0 | 0 | 0 | — | 70 | 0 | 0 | 0 | 0 |
| 173 | — | 95 | 30 | 0 | 0 | 0 | 0 | — | 20 | 0 | 0 | 0 | 0 |
| 174 | — | 98 | 60 | 20 | 0 | 0 | 0 | — | 40 | 0 | 0 | 0 | 10 |
| 175 | — | 98 | 98 | 30 | 0 | 0 | 0 | — | 60 | 10 | 0 | 0 | 0 |
| 176 | — | 99 | 98 | 80 | 40 | 0 | 20 | — | 70 | 10 | 0 | 0 | 10 |
| 177 | — | 100 | 100 | 20 | 90 | 30 | 20 | — | 98 | 20 | 10 | 10 | 20 |
| 178 | — | 98 | 98 | 30 | 97 | 0 | 20 | — | 90 | 30 | 0 | 0 | 0 |
| 179 | — | 98 | 70 | 0 | 0 | 0 | 0 | — | 60 | 0 | 0 | 0 | 0 |
| 180 | — | 99 | 99 | 10 | 80 | 20 | 30 | — | 95 | 0 | 20 | 40 | 0 |
| 181 | — | 30 | 50 | 20 | 90 | 100 | 0 | — | 90 | 98 | 100 | 100 | 100 |
| 182 | — | 100 | 100 | 80 | 40 | 30 | 70 | — | 0 | 0 | 0 | 0 | 0 |

Percent Control at 2 lb/A

| Compound Number | Pre-emergence | | | | | | Post-emergence | | | | | |
| --- | --- | --- | --- | --- | --- | --- | --- | --- | --- | --- | --- | --- |
| | CG | FT | WG | WO | MD | CD | PW | CG | FT | WG | WO | MD | CD | PW |
| 183 | — | 80 | 98 | 80 | 10 | 0 | 10 | — | 80 | 80 | 20 | 20 | 0 | 10 |
| 184 | — | 100 | 100 | 100 | 10 | 98 | 90 | — | 99 | 95 | 70 | 100 | 98 | 100 |
| 185 | — | 100 | 100 | 100 | 98 | 99 | 100 | — | 80 | 90 | 20 | 20 | 30 | 0 |
| 186 | — | 20 | 10 | 10 | 0 | 0 | 0 | — | 0 | 0 | 0 | 0 | 0 | 0 |
| 187 | — | 100 | 100 | 10 | 0 | 20 | 0 | — | 80 | 90 | 10 | 50 | 50 | 20 |
| 188 | — | 99 | 96 | 80 | 0 | 0 | 0 | — | 20 | 20 | 0 | 0 | 0 | 0 |
| 189 | — | 100 | 98 | 40 | 0 | 0 | 0 | — | 50 | 40 | 0 | 0 | 0 | 0 |
| 190 | — | 0 | 20 | 0 | 0 | 0 | 0 | — | 0 | 0 | 0 | 0 | 0 | 0 |
| 191 | — | 98 | 98 | 20 | 0 | 40 | 0 | — | 60 | 80 | 0 | 0 | 0 | 0 |
| 192 | — | 100 | 100 | 80 | 20 | 80 | 60 | — | 80 | 80 | 10 | 0 | 0 | 0 |
| 193 | — | 100 | 100 | 60 | 0 | 0 | 0 | — | 30 | 40 | 0 | 0 | 0 | 0 |
| 194 | — | 20 | 60 | 0 | 0 | 0 | 0 | — | 0 | 0 | 0 | 0 | 0 | 0 |
| 195 | — | 20 | 60 | 0 | 0 | 0 | 0 | — | 0 | 0 | 0 | 0 | 0 | 0 |
| 196 | — | 0 | 0 | 0 | 0 | 0 | 0 | — | 20 | 0 | 0 | 0 | 0 | 0 |
| 197 | — | 10 | 10 | 0 | 0 | 0 | 0 | — | 0 | 0 | 0 | 0 | 0 | 0 |
| 198 | — | 40 | 60 | 0 | 0 | 0 | 0 | — | 20 | 20 | 0 | 0 | 0 | 0 |
| 199 | — | 100 | 100 | 70 | 20 | 98 | 40 | — | 90 | 90 | 30 | 40 | 40 | 30 |
| 200 | — | 0 | 0 | 0 | 0 | 0 | 0 | — | 80 | 60 | 0 | 10 | 70 | 20 |
| 201 | — | 30 | 80 | 10 | 0 | 0 | 0 | — | 80 | 80 | 20 | 30 | 30 | 10 |
| 202 | — | 0 | 0 | 0 | 0 | 0 | 0 | — | 80 | 40 | 0 | 20 | 70 | 40 |
| 203 | — | 100 | 100 | 98 | 30 | 98 | 0 | — | 90 | 80 | 20 | 30 | 50 | 50 |
| 204 | — | 100 | 100 | 90 | 30 | 80 | 0 | — | 90 | 80 | 20 | 30 | 60 | 0 |
| 205 | — | 100 | 100 | 80 | 0 | 90 | 98 | — | 70 | 80 | 20 | 20 | 30 | 20 |
| 206 | — | 100 | 100 | 80 | 95 | 98 | 30 | — | 80 | 80 | 10 | 30 | 20 | 100 |
| 207 | — | 100 | 100 | 80 | 60 | 100 | 100 | — | 80 | 80 | 80 | 40 | 60 | 20 |
| 208 | — | 100 | 100 | 60 | 20 | 100 | 100 | — | 80 | 60 | 0 | 0 | 0 | 0 |
| 209 | — | 40 | 0 | 0 | 50 | 60 | 90 | — | 0 | 0 | 40 | 40 | 60 | 40 |
| 210 | — | 100 | 100 | 100 | 60 | 100 | 100 | — | 0 | 0 | 0 | 0 | 0 | 0 |
| 211 | — | 98 | 98 | 70 | 0 | 80 | 80 | — | 60 | 40 | 50 | 60 | 75 | 60 |
| 212 | — | 70 | 50 | 0 | 0 | 40 | 0 | — | 60 | 0 | 0 | 70 | 70 | 60 |

Percent Control at 8 lb/A

| Compound Number | Pre-emergence | | | | | | | Post-emergence | | | | | |
| --- | --- | --- | --- | --- | --- | --- | --- | --- | --- | --- | --- | --- | --- |
| | CG | FT | WG | RO | PW | MD | CD | CG | WG | RO | MD | CD | BN |
| 213 | 98 | 99 | 99 | 40 | 0 | 0 | 40 | 95 | 95 | 20 | 10 | 20 | 30 |
| 214 | 100 | 100 | 100 | 20 | 90 | 30 | 85 | 95 | 90 | 0 | 0 | 20 | 50 |
| 215 | 100 | 100 | 100 | 98 | 80 | 60 | 95 | 100 | 95 | 20 | 0 | 0 | 50 |
| 216 | 100 | 100 | 100 | 60 | 80 | 30 | 80 | 100 | 95 | 0 | 0 | 0 | 40 |
| 217 | 100 | 99 | 99 | 50 | 90 | 10 | 60 | 0 | 0 | 0 | 0 | 0 | 0 |
| 218 | 100 | 99 | 99 | 99 | 90 | 10 | 80 | 90 | 80 | 0 | 0 | 0 | 20 |
| 219 | 100 | 100 | 100 | 100 | 90 | 60 | 80 | 95 | 90 | 20 | 0 | 0 | 0 |
| 220 | 100 | 100 | 100 | 98 | 98 | 20 | 90 | 20 | 0 | 0 | 60 | 0 | 20 |
| 221 | 100 | 100 | 100 | 70 | 90 | 60 | 95 | 98 | 90 | 0 | 20 | 30 | 50 |
| 222 | 100 | 100 | 100 | 98 | 99 | 97 | 98 | 95 | 80 | 70 | 40 | 80 | 98 |
| 223 | 99 | 97 | 98 | 60 | 30 | 0 | 60 | 100 | 90 | 0 | 0 | 100 | 40 |
| 224 | 100 | 98 | 98 | 95 | 50 | 30 | 40 | 98 | 90 | 20 | 10 | 40 | 40 |
| 225 | 100 | 99 | 95 | 60 | 30 | 0 | 40 | 98 | 95 | 20 | 10 | 40 | 40 |
| 226 | 98 | 98 | 80 | 0 | 0 | 0 | 0 | 98 | 30 | 0 | 30 | 40 | 50 |
| 227 | 98 | 98 | 30 | 0 | 0 | 0 | 0 | 80 | 20 | 0 | 0 | 0 | 40 |
| 228 | 98 | 98 | 95 | 20 | 0 | 0 | 0 | 98 | 30 | 0 | 0 | 0 | 30 |
| 229 | 99 | 98 | 98 | 98 | 0 | 0 | 0 | 99 | 90 | 30 | 0 | 50 | 30 |
| 230 | 98 | 80 | 80 | 80 | 0 | 0 | 0 | 98 | 90 | 10 | 0 | 100 | 40 |
| 231 | 0 | 0 | 0 | 0 | 0 | 0 | 0 | 90 | 0 | 0 | 0 | 0 | 0 |

TABLE II-continued
Herbicidal Activity - Screening Results

| | | | | | | | | | | | | | | |
|---|---|---|---|---|---|---|---|---|---|---|---|---|---|---|
| 232 | 98 | 96 | 98 | 97 | 0 | 0 | 0 | 95 | 70 | 20 | 0 | 30 | 30 | |
| 233 | 100 | 100 | 100 | 98 | 70 | 70 | 60 | 98 | 80 | 10 | 40 | 20 | 40 | |
| 234 | 100 | 100 | 100 | 99 | 99 | 95 | 90 | 98 | 95 | 20 | 30 | 100 | 80 | |
| 235 | — | 100 | 100 | 95 | 90 | 95 | 99 | — | 80 | 10 | 50 | 60 | 20 | |
| 236 | — | 100 | 100 | 99 | 99 | 96 | 99 | — | 85 | 20 | 40 | 40 | 50 | |
| 237 | — | 99 | 99 | 40 | 95 | 30 | 95 | — | 60 | 0 | 0 | 0 | 5 | |
| 238 | — | 100 | 100 | 95 | 40 | 30 | 90 | — | 80 | 0 | 0 | 40 | 40 | |
| 239 | — | 95 | 98 | 20 | 80 | 60 | 70 | — | 0 | 0 | 0 | 0 | 10 | |
| 240 | — | 100 | 100 | 95 | 40 | 60 | 90 | — | 30 | 0 | 0 | 100 | 40 | |
| 241 | — | 80 | 95 | 0 | 0 | 0 | 0 | — | 0 | 0 | 0 | 0 | 10 | |
| 242 | — | 100 | 100 | 98 | 95 | 10 | 80 | — | 30 | 0 | 0 | 0 | 30 | |
| 243 | — | 0 | 10 | 10 | 0 | 0 | 0 | — | 0 | 0 | 0 | 0 | 10 | |
| 244 | — | 40 | 40 | 0 | 0 | 0 | 0 | — | 0 | 0 | 0 | 0 | 0 | |
| 245 | — | 95 | 95 | 10 | 0 | 0 | 0 | — | 0 | 0 | 0 | 0 | 0 | |
| 246 | — | 90 | 98 | 20 | 60 | 0 | 0 | — | 60 | 0 | 0 | 30 | 0 | |
| 247 | — | 99 | 95 | 40 | 30 | 0 | 0 | — | 0 | 0 | 0 | 0 | 0 | |
| 248 | — | 30 | 0 | 0 | 0 | 0 | 0 | — | 0 | 0 | 0 | 0 | 0 | |
| 249 | — | 98 | 98 | 40 | 0 | 0 | 0 | — | 40 | 0 | 0 | 0 | 10 | |
| 250 | — | 99 | 100 | 0 | 30 | 40 | 40 | — | 60 | 0 | 0 | 0 | 0 | |
| 251 | — | 98 | 97 | 40 | 0 | 0 | 0 | — | 60 | 0 | 0 | 0 | 40 | |
| 252 | — | 100 | 100 | 98 | 80 | 90 | 97 | — | 70 | 0 | 40 | 0 | 20 | |
| 253 | — | 100 | 100 | 100 | 98 | 98 | 98 | — | 70 | 0 | 30 | 0 | 40 | |
| 254 | — | 80 | 70 | 30 | 0 | 0 | 0 | — | 0 | 0 | 0 | 0 | 0 | |
| 255 | — | 80 | 70 | 40 | 0 | 0 | 0 | — | 20 | 0 | 0 | 0 | 40 | |
| 256 | — | 100 | 100 | 99 | 98 | 98 | 98 | — | 80 | 0 | 40 | 30 | 30 | |
| 257 | — | 100 | 100 | 100 | 99 | 98 | 98 | — | 70 | 0 | 30 | 0 | 50 | |
| 258 | — | 100 | 100 | 30 | 0 | 0 | 0 | — | 40 | 0 | 0 | 0 | 0 | |
| 259 | — | 100 | 100 | 30 | 20 | 0 | 0 | — | 70 | 0 | 30 | 0 | 50 | |
| 260 | — | 100 | 100 | 50 | 80 | 60 | 80 | — | 60 | 0 | 30 | 0 | 30 | |
| 261 | — | 100 | 100 | 40 | 60 | 50 | 30 | — | 70 | 0 | 20 | 0 | 60 | |
| 262 | — | 100 | 100 | 60 | 80 | 60 | 95 | — | 0 | 0 | 0 | 0 | 30 | |
| 263 | — | 100 | 100 | 70 | 90 | 90 | 95 | — | 30 | 0 | 0 | 0 | 20 | |
| 264 | — | 0 | 40 | 10 | 0 | 0 | 0 | — | 0 | 0 | 0 | 0 | 0 | |
| 265 | — | 98 | 98 | 97 | 0 | 0 | 0 | — | 0 | 0 | 0 | 0 | 0 | |
| 266 | — | 100 | 100 | 98 | 80 | 80 | 98 | — | 80 | 0 | 50 | 0 | 30 | |
| 267 | — | 100 | 100 | 90 | 60 | 80 | 95 | — | 80 | 0 | 50 | 0 | 60 | |
| 268 | — | 70 | 80 | 40 | 0 | 0 | 0 | — | 0 | 0 | 0 | 0 | 0 | |
| 269 | — | 80 | 90 | 10 | 30 | 0 | 20 | — | 0 | 0 | 0 | 0 | 0 | |
| 270 | — | 0 | 70 | 0 | 0 | 0 | 0 | — | 0 | 0 | 0 | 0 | 0 | |
| 271 | — | 100 | 100 | 100 | 50 | 90 | 50 | — | 80 | 20 | 0 | 0 | 30 | |
| 272 | — | 100 | 95 | 20 | 0 | 0 | 0 | — | 0 | 0 | 0 | 0 | 0 | |
| 273 | — | 100 | 100 | 30 | 0 | 0 | 0 | — | 40 | 0 | 70 | 0 | 0 | |
| 274 | — | 95 | 90 | 80 | 50 | 70 | 20 | — | 0 | 0 | 0 | 0 | 0 | |
| 275 | — | 100 | 100 | 100 | 80 | 80 | 80 | — | 80 | 20 | 10 | 10 | 0 | |
| 276 | — | 50 | 0 | 0 | 0 | 0 | 0 | — | 0 | 0 | 0 | 0 | 0 | |
| 277 | — | 99 | 98 | 10 | 40 | 0 | 40 | — | 80 | 20 | 10 | 10 | 30 | |
| 278 | — | 99 | 96 | 30 | 0 | 0 | 0 | — | 70 | 10 | 0 | 0 | 50 | |
| 279 | — | 98 | 98 | 30 | 0 | 0 | 0 | — | 0 | 0 | 0 | 0 | 0 | |
| 280 | — | 60 | 95 | 20 | 0 | 0 | 0 | — | 0 | 0 | 0 | 0 | 0 | |
| 281 | — | 95 | 10 | 0 | 0 | 0 | 0 | — | 50 | 0 | 0 | 0 | 0 | |
| 282 | — | 20 | 0 | 0 | 0 | 0 | 0 | — | 0 | 0 | 0 | 0 | 0 | |
| 283 | — | 100 | 100 | 100 | 100 | 100 | 100 | — | 90 | 60 | 100 | 90 | 100 | |
| 284 | — | 100 | 100 | 100 | 100 | 99 | 99 | — | 90 | 60 | 80 | 100 | 30 | |

| Compound | Percent Control at 2 lb/A | | | | | | | | | | | | |
|---|---|---|---|---|---|---|---|---|---|---|---|---|---|
| | Pre-emergence | | | | | | | Post-emergence | | | | | |
| Number | CG | FT | WG | WO | MD | CD | PW | CG | FT | WG | WO | MD | CD | PW |
| 285 | — | 100 | 100 | 30 | 10 | 90 | 60 | — | 90 | 90 | 40 | 40 | 40 | 0 |
| 286 | — | 100 | 40 | 10 | 80 | 80 | 20 | — | 40 | 40 | 20 | 80 | 70 | 0 |
| 287 | — | 100 | 100 | 95 | 95 | 100 | 100 | — | 98 | 70 | 60 | 75 | 70 | 100 |
| 288 | — | 100 | 100 | 100 | 85 | 100 | 100 | — | 75 | 80 | 75 | 60 | 70 | 0 |
| 289 | — | 100 | 100 | 98 | 80 | 100 | 100 | — | 60 | 70 | 50 | 40 | 75 | 0 |
| 290 | — | 100 | 100 | 98 | 98 | 100 | 100 | — | 65 | 70 | 50 | 40 | 60 | 30 |
| 291 | — | 100 | 100 | 100 | 95 | 100 | 100 | — | 75 | 75 | 60 | 30 | 60 | 0 |
| 292 | — | 100 | 100 | 100 | 95 | 100 | 100 | — | 70 | 75 | 60 | 60 | 70 | 50 |
| 293 | — | 100 | 100 | 100 | 98 | 100 | 100 | — | 80 | 75 | 60 | 60 | 60 | 30 |
| 294 | — | 100 | 100 | 95 | 90 | 100 | 100 | — | 70 | 75 | 75 | 60 | 60 | 100 |

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity.

Useful formulations of the compounds of the present invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volume of from a few liters to several hundred liters per hectare. High strength compositions are priaarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 5-50 | 40-95 | 0-15 |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or high levels of active ingredient can, of course, be present depending on the intended use and the physical properties of the compound. Higher ratios of surfactant to active ingredient are sometimes desirable, and are achieved by incorporation into the formulation or by tank mixing.

Compositions including active compounds also may be applied by addition to irrigation waters supplied to the field to be treated. This method of application permits penetration of the compounds into the soil as the water is absorbed therein. Compositions applied to the surface of the soil can be incorporated and distributed below the surface of the soil by conventional means such as discing or mixing operations.

The compositions can also comprise such additional Substances as other pesticides, such as insecticides, nematocides, fungicides, and the like; stabilizers, spreaders, deactivators, adhesives, stickers, fertilizers, activators, synergists, antidotes, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides.

The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, sifuron, dichloral urea, chloroxuron, cycluron, fenuron, monuron, monuron TCA, diuron, linuron, monolinuron neburon, buturon, trimethuron and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as 4-(chloroacetyl)-morpholine, 1-(chloroacetyl)-piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichloro-phenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamide, dipropalin, trifluralin, solan, dicryl, merphos, DMPA, DSMA, MSMA, pottasium azide, acrolein, benefin, bensulide, AMS, bromacil, 2-(3,4-dichlorophenyl)-4-methyl-1,2,4-oxazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no relative economic value, and interfering with the production of cultivated crops, with the growing of ornamental plants, or with the welfare of livestock.

Similarly, such weeds can be classified as broadleaf or grassy weeds. it is economically desirable to control the growth of such weeds without damaging beneficial plants or livestock.

What is claimed is:

1. A compound having the formula

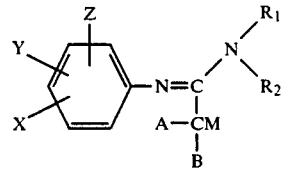

in which
R₁ is hydrogen;
R₂ is alkyl having 1-6 carbon atoms, inclusive;
—CMAB is CHCl₂;
X and Y are independently selected from the group consisting of lower alkyl having 1 to 6 carbon atoms, inclusive, and chloro; and
Z is hydrogen.

2. A compound according to claim 1 in which
R₁ is hydrogen;
R₂ is alkyl having 1 to 6 carbon atoms, inclusive;
—CMAB is —CHCl₂;
X is chloro;
Y is chloro;

Z is hydrogen.
3. A compound according to claim 2 in which
R$_2$ is isopropyl;
X is 3-chloro;
Y is 5-chloro.
4. A compound according to claim 2 in which
R$_2$ is isopropyl;
X is 2-chloro;
Y is 3-chloro.
5. A compound according to claim 2 in which
R$_2$ is ethyl;
X is 3-chloro;
Y is 4-chloro.
6. A compound according to claim 2 in which
R$_2$ is n-propyl;
X is 3-chloro;
Y is 4-chloro.
7. A compound according to claim 2 in which
R$_2$ is isopropyl;
X is 3-chloro;
Y is 4-chloro.
8. A compound according to claim 1 in which
R$_1$ is hydrogen;
R$_2$ is alkyl having 1 to 6 carbon atoms, inclusive;
—CMAB is —CHCl$_2$;
X is lower alkyl having 1 to 6 carbon atoms, inclusive;
Y is lower alkyl having 1 to 6 carbon atoms, inclusive;
Z is hydrogen.
9. A compound according to claim 8 in which
R$_2$ is isopropyl;
X is 3-methyl;
Y is 5-methyl.
10. A compound having the formula

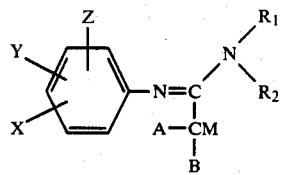

in which
R$_1$ is hydrogen;
R$_2$ is alkyl having 1-6 carbon atoms, inclusive;
—CMAB is CHCl$_2$;
X is lower alkyl having 1 to 6 carbon atoms, inclusive;
Y is chloro; and
Z is hydrogen.
11. A compound according to claim 10 in which
R$_2$ is isopropyl;
X is 2-methyl;
Y is 3-chloro.
12. A compound having the formula

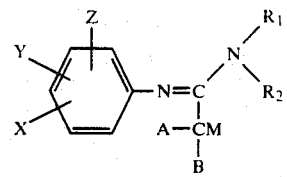

in which
R$_1$ is allyl;
R$_2$ is allyl;
—CMAB is CHCl$_2$;
X is chloro;
Y is chloro; and
Z is hydrogen.
13. A compound having the formula

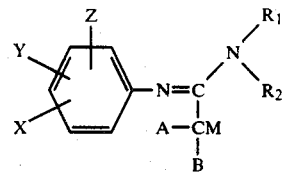

in which
R$_1$ is hydrogen;
R$_2$ is alkyl having 1-6 carbon atoms, inclusive;
—CMAB is CHF$_2$;
X is chloro;
Y is chloro; and
Z is hydrogen.
14. A compound according to claim 13 in which
X is 3-chloro;
Y is 5-chloro;
R$_2$ is isopropyl.

* * * * *